(12) United States Patent
Wang et al.

(10) Patent No.: US 12,151,140 B2
(45) Date of Patent: Nov. 26, 2024

(54) TECHNIQUES FOR PROVIDING CUSTOMIZED EXERCISE-RELATED RECOMMENDATIONS

(71) Applicant: Apple Inc., Cupertino, CA (US)

(72) Inventors: Ying Wang, Arlington, VA (US); Robert Pitchford, San Jose, CA (US); Stephen Holter, Morgan Hill, CA (US)

(73) Assignee: Apple Inc., Cupertino, CA (US)

( * ) Notice: Subject to any disclaimer, the term of this patent is extended or adjusted under 35 U.S.C. 154(b) by 593 days.

(21) Appl. No.: 17/026,011

(22) Filed: Sep. 18, 2020

(65) Prior Publication Data

US 2021/0001180 A1    Jan. 7, 2021

Related U.S. Application Data

(63) Continuation of application No. 15/625,849, filed on Jun. 16, 2017, now Pat. No. 10,814,170.

(51) Int. Cl.
| | |
|---|---|
| *A63B 24/00* | (2006.01) |
| *G06N 20/00* | (2019.01) |
| *G16H 20/30* | (2018.01) |
| *A63B 21/06* | (2006.01) |
| *A63B 22/00* | (2006.01) |
| *A63B 22/06* | (2006.01) |

(52) U.S. Cl.
CPC ......... *A63B 24/0075* (2013.01); *G06N 20/00* (2019.01); *G16H 20/30* (2018.01); *A63B 21/06* (2013.01); *A63B 22/0076* (2013.01); *A63B 22/0605* (2013.01); *A63B 22/0664* (2013.01); *A63B 24/0062* (2013.01); *A63B 2024/0068* (2013.01); *A63B 2024/0081* (2013.01); *A63B 2220/40* (2013.01); *A63B 2220/803* (2013.01);

(Continued)

(58) Field of Classification Search
None
See application file for complete search history.

(56) References Cited

U.S. PATENT DOCUMENTS

| | | |
|---|---|---|
| 6,601,016 B1 | 7/2003 | Brown et al. |
| 8,172,724 B2 | 5/2012 | Solomon |

(Continued)

FOREIGN PATENT DOCUMENTS

| | | |
|---|---|---|
| CN | 103403723 A | 11/2013 |
| CN | 105190626 A | 12/2015 |

(Continued)

OTHER PUBLICATIONS

Jiang et al., "Maximizing Customer Satisfaction Through An Online Recommendation System: A Novel Associative Classification Mode", Decision Support System, Elsevier Science Publishers, vol. 48, Issue No. 3, 2010, pp. 470-479.

(Continued)

*Primary Examiner* — James B Hull
(74) *Attorney, Agent, or Firm* — Kilpatrick Townsend & Stockton LLP

(57) ABSTRACT

A classification model is generated based on historical exercise information. User exercise information is classified into an exercise category using the classification model. Recommendations based on the exercise category is identified. A customized exercise recommendation is determined from the identified recommendations based on a comparison of the user exercise information and expected progress data. This customized recommendation is provided to a user device for consumption.

20 Claims, 8 Drawing Sheets

(52) U.S. Cl.
CPC ..... *A63B 2220/833* (2013.01); *A63B 2225/20* (2013.01); *A63B 2230/06* (2013.01)

(56) References Cited

U.S. PATENT DOCUMENTS

| | | | |
|---|---|---|---|
| 9,330,239 | B2 | 5/2016 | Koduri et al. |
| 2015/0005911 | A1* | 1/2015 | Lake, II ................ A63B 71/06 700/91 |
| 2015/0080184 | A1 | 3/2015 | Boyette |
| 2016/0325140 | A1 | 11/2016 | Wu |
| 2017/0007885 | A1 | 1/2017 | Kerwin |

FOREIGN PATENT DOCUMENTS

| | | |
|---|---|---|
| CN | 106537397 A | 3/2017 |
| WO | 03/079134 A2 | 9/2003 |

OTHER PUBLICATIONS

International Patent Application No. PCT/US2018/022206, "International Search Report and Written Opinion Received", Jun. 11, 2018, 15 pages.

Timofeev, Ivan et al., "Training Assistant: the Automatic Training Data Collection System," Proceeding of the 16$^{th}$ Conference of Fruct Association, 2014. Downloaded from: https://fruct.org/publications/abstract16/files/Tim.pdf. 1 page.

"International Preliminary Report on Patentability," mailed Dec. 26, 2019 in International Application No. PCT/US2018/022206. 11 pages.

"Notice of Allowance," mailed Jun. 24, 2020 in U.S. Appl. No. 15/625,849. 16 pages.

"Non-Final Office Action," mailed Nov. 13, 2019 in U.S. Appl. No. 15/625,849. 16 pages.

Kunden, Mehr et al., "eGym is the new, fascinating training concept." 2015. 152 pages (includes English translation).

* cited by examiner

TECHNIQUES FOR PROVIDING CUSTOMIZED EXERCISE-RELATED RECOMMENDATIONS

CROSS-REFERENCES TO RELATED APPLICATIONS

This application is a continuation of U.S. application Ser. No. 15/625,849, filed Jun. 16, 2017 (now U.S. Pat. No. 10,814,170, issued Oct. 27, 2020) entitled, "Techniques for Providing Customized Exercise-Related Recommendation," which is hereby incorporated by reference in its entirety for all purposes.

BACKGROUND

As individuals are devoting more and more time to non-physical activities, and as the rates of obesity and disease are on the rise, the need for greater amounts of physical exercise is a reality for many. It is often difficult for a person to educate himself with respect to proper exercise, as conflicting information is widespread. For those with the financial means and desire, a personal trainer or a health coach can be excellent resource for achieving fitness goals. However, the costs associated with utilizing a personal trainer or health coach may be prohibitive for many people. Many individuals are turning to health and fitness devices to help track their health and fitness progress. Although health and fitness devices provide some feedback, these devices do not provide the level of customized support and advice that one would receive from a personal trainer, as such devices are often limited to processing particular types of data (e.g., feedback from onboard sensors, user input, etc.). Similarly, exercise machines such as stationary bikes, weight lifting machines, treadmill machines, elliptical machines, and the like, often provide exercise feedback to the user during an exercise session. However, such feedback is often transitory or underutilized in conventional health and fitness systems.

SUMMARY

Embodiments of the present disclosure can provide systems, methods, and computer-readable medium for providing customized exercise-related recommendations.

In some embodiments, a computer-implemented method for providing customized exercise-related recommendations may be provided. The method may comprise identifying, by a service provider processing device, user interactions with a particular exercise machine of a plurality of exercise machines, the user interactions associated with a user profile, each of the plurality of exercise machines comprising a computing device in communication with the server provider processing device. The method may further comprise obtaining, by the service provider processing device, exercise information corresponding to a plurality of user profiles, the exercise information being obtained from the plurality of exercise machines. The method may further comprise generating, by the service provider processing device, a classification model based on the exercise information corresponding to the plurality of user profiles. The method may further comprise receiving, by the service provider processing device, exercise metrics associated with the user interactions with the particular exercise machine. The method may further comprise determining, by the service provider processing device, an exercise category for the user profile based on the classification model and at least one of the exercise metrics and the user profile. The method may further comprise identifying, by the service provider processing device, a plurality of exercise recommendations based on the exercise category. The method may further comprise identifying, by the service provider processing device, a customized exercise recommendation from the plurality of exercise recommendations based on comparing the exercise metrics to expected progress data. The method may further comprise providing, by the service provider processing device, the customized exercise recommendation to a user device associated with the user profile.

In some embodiments, a system for providing customized exercise-related recommendations may be provided. The system may comprise a plurality of exercise machines individually configured with one or more sensors, one or more data networks, one or more processors, and one or more memories storing computer-readable instructions. Executing the instructions (by the one or more processors) may cause the system to at least collect, at an exercise machine, exercise information for a plurality of user workout sessions, wherein the exercise information comprises a duration of a workout, a level of workout, or a number of repetitions performed. Executing the instructions may further cause the system to identify a first user workout session of the plurality of user workout sessions. Executing the instructions may further cause the system to identify first user information corresponding to the first user workout session. Executing the instructions may further cause the system to access the collected exercise information. Executing the instructions may further cause the system to identify a plurality of exercise recommendations based on the first user information and the collected exercise information. Executing the instructions may further cause the system to determine a customized exercise recommendation from a plurality of recommendations based on the first user information and a comparison between the collected exercise information and expected progress data. Executing the instructions may further cause the system to present the customized exercise recommendation.

In some embodiments, a computer-readable medium may be provided. The computer-readable medium may include computer-executable instructions that, when executed by a processor, cause the processor to perform operations. The operations may comprise obtaining a classification model for determining a first user exercise category, the classification model being previously-generated based on collected exercise information of a plurality of user workout sessions. The operations may further comprise identifying first user profile information. The operations may further comprise receiving first user exercise information related to an exercise machine. The operations may further comprise identifying a plurality of exercise recommendations based on the first user exercise category. The operations may further comprise determining a customized exercise recommendation from the plurality of exercise recommendations based on a comparison of the first user exercise information to expected progress data. The operations may further comprise providing the customized exercise recommendation.

The following detailed description together with the accompanying drawings will provide a better understanding of the nature and advantages of the present disclosure.

BRIEF DESCRIPTION OF THE DRAWINGS

Various embodiments in accordance with the present disclosure will be described with reference to the drawings, in which.

DETAILED DESCRIPTION

Figure 1:
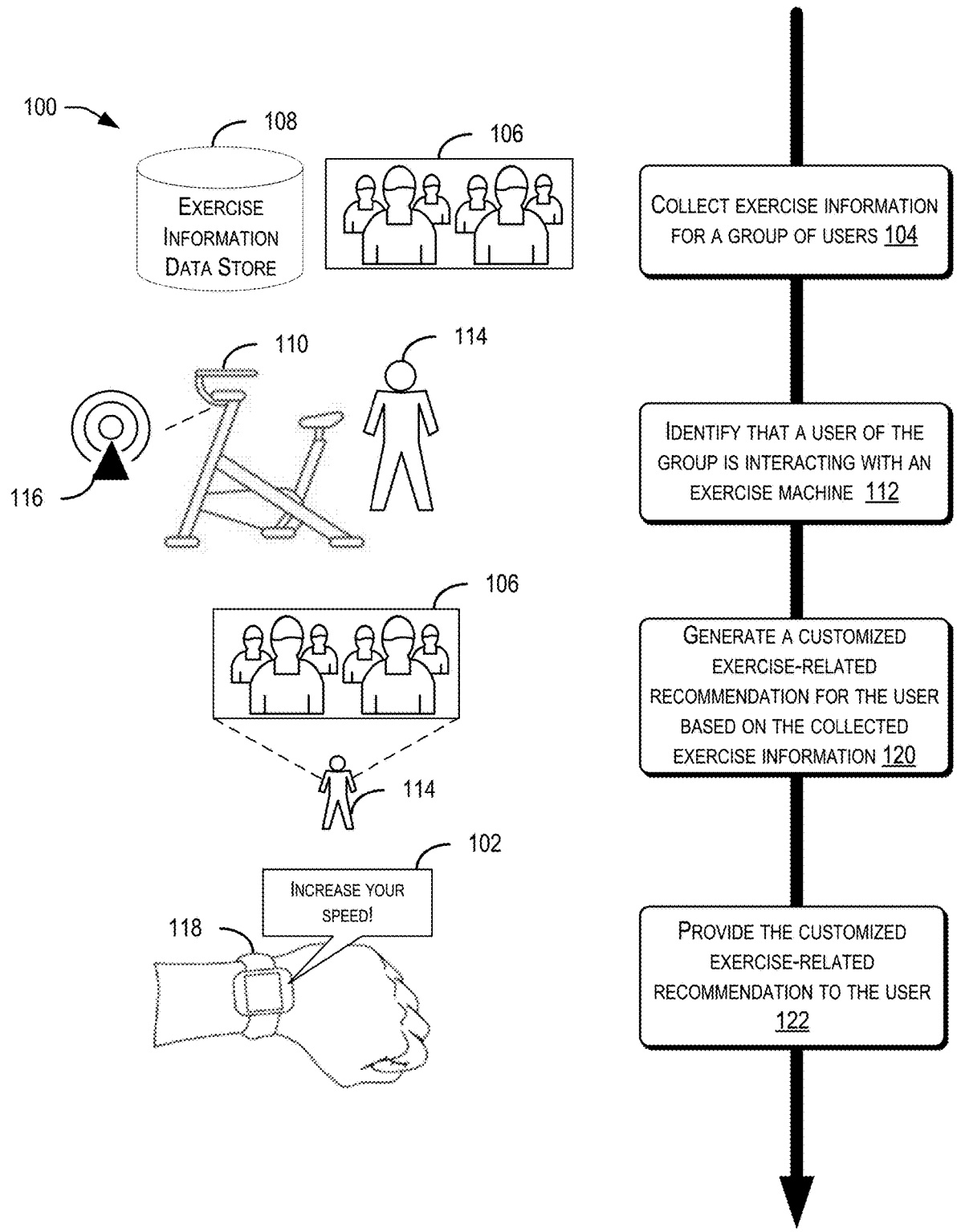
FIG. 1 is a simplified block diagram illustrating an example flow for providing a customized exercise-related recommendation, according to at least one embodiment.

Certain embodiments of the present disclosure relate to devices, computer-readable medium, systems, and methods for providing customized exercise-related recommendations (e.g., recommendations that are customized with respect to a particular individual). Although examples herein may specifically focus on exercise-related recommendations, it should be appreciated that similar techniques may be utilized to provide other types of customized recommendations including, but not limited to, health and fitness-related recommendations (e.g., "drink more water," "ingest more protein," "get more sleep," "reduce your sugar intake," etc.) or any other type of recommendations. An "exercise recommendation" can include any suitable suggestion related to exercise (e.g., a change in a type of exercise machine utilized by a user and/or the manner in which a user utilizes a particular exercise machine). By way of example, an exercise recommendation may suggest a change in speed, weight, repetition, form, type of exercise machine, or any suitable characteristic related to a user's utilization of one or more exercise machines. An exercise machine may be any suitable electronic or non-electronic device, combination of devices, or instruments that is suitable for use in an exercise. Examples of exercise machines include stationary machines, weight lifting machine, fitness balls, tension cords, etc.). In at least some examples, an exercise machine may include (or be otherwise in communication with) one or more sensors (e.g., accelerometers, gyroscopes, cameras, blood pressure sensors, oxygen sensors, heartrate sensors, thermometers, etc.).

It should be appreciated that any information discussed herein may be collected in situations in which the user has approved collection and/or utilization of such information. A user may be provided the opportunity to opt-in and/or opt-out of the services discussed below. Any information collected and/or utilized may be securely maintained and may not be shared with other parties. The user may choose to opt-out of the services discussed herein at any suitable time.

Generally, by utilizing the techniques described herein, an exercise recommendation engine may provide customized exercise-related recommendations to a user. While conventional systems may provide generic recommendations, such systems do not collect and/or utilize data related to other users when determining specific recommendations to provide to a particular user. The techniques discussed herein train a classification model utilizing specific inputs (e.g., fitness-related information that includes exercise information, vital sign information, and/or user profile information) related to a group of users/user profiles. Once trained, input data (e.g., fitness-related information of a single user) may be provided to the classification model. The classification model may produce output indicating at least a classification for the input data. A recommendation corresponding to the classification may be identified and provided to the user. By classifying the input data, and matching the classification to a recommendation, the recommendation provided is more likely to be applicable to the user and/or more effective at bringing about a desired result (e.g., the user meeting a user-defined, system-defined, and/or pre-defined fitness goal).

Additionally, user compliance with recommendations may be tracked such that over time, the system may learn to: 1) more accurately classify input data, 2) provide increasingly effective recommendations to progress the user toward a user-defined and/or system-defined fitness goal, and/or 3) adjust expected progress data to provide increasingly realistic progress paths by which users are expected to progress toward a fitness goal. For example, the system may determine that previously provided recommendations have not produced a desired result (e.g., over a threshold number of times). In some embodiments, the system may retrain the classification engine using more recent data, adjust expected progress data, and/or adjust which recommendations are provided (e.g., by adjusting the classification associated with a recommendation), or any suitable combination of the above. Thus, the system may adjust over time, such that classification, recommendation, and progress path accuracy/effectiveness may be improved.

By way of example, exercise information corresponding to a group of users may be collected and utilized to provide exercise-related recommendations that are customized for a particular user. Exercise information (e.g., collected during a user's workout session) may include any suitable data obtainable from one or more sensors (e.g., an accelerometer, a gyroscope, a camera, etc.) attached to, or otherwise in communication with, an exercise machine or user device (e.g., a body-worn device, a cellphone, etc.). Exercise information may additionally, or alternatively, include machine identification data (e.g., a machine identifier), or any suitable information related to an exercise machine and/or a measure corresponding to an exercise performed at the exercise machine. A user's workout session may include exercise information from one or more exercise machines over a period of time (e.g., 1 hour, 3 hours, 1 day, 2 months, 5 years, etc.). Exercise information may be utilized to determine a myriad of metrics such as a speed, an amount of weight being lifted, a range of motion associated with a part of an exercise machine, an amount of shaking associated with one or more parts of the exercise machine and/or user, a number of repititions performed, and the like. Collectively, exercise information associated with a group of users may be utilized to provide customized recommendations to registered and unregistered users alike, as will be discussed in more detail below.

In some embodiments, user profile information may be collected during a registration process or at any suitable time. User-profile information may be received as user input and may include any suitable information associated with a user including, but is not limited to, physical characteristics (weight, height, body type, physical disability, dietary/nutritional considerations, general activity level (e.g., sedentary, active), etc.) demographic information (e.g., age, gender, ethinicity, etc.), medical information (e.g., a medical diagnosis, a medication currently being taken, a dosage for such medication(s), a genetic disposition to a particular disease/disorder, etc.), goal information (e.g., identifying one or more fitness goals such as running a full marathon, building strength in a particular muscle group, physical therapy goals, running a 5K, being able to run for 30 minutes straight, running a mile in under 6 minutes, etc.), and the like.

In some embodiments, a fitness goal may be associated with an improvement related to weight loss (generally, or a specific amount), strength training (generally, or with respect to a particular muscle group and/or body part), stamina building (generally, or as indicated by a particular speed/duration/distance desired), general and/or specific health concerns (such cardiofascular improvements, disease prevention, physical therapy, etc.), and the like. User profile information may further include metrics collected by a user device (e.g., a pedometer, an accelerometer) indicating a general activity level. Collectively, user profile information for a group of users may be utilized to provide customized recommendations to registered and unregistered users alike, as will be discussed in more detail below.

In still further examples, vital sign information may be received and stored. The vital sign information may be collected by any suitable sensor configured to measure vital signs of a user (e.g., a heart rate, an oxygen level, blood pressure, temperature, etc.). In some embodiments, one or more sensors for measuring vital signs may be attached to a user device and/or to an exercise machine. Collectively, vital sign information associated with individuals of a group of users may be utilized to provide customized recommendations to registered and unregistered users alike, as will be discussed in more detail below.

In at least one embodiment, a user may be classified as a particular type of user (e.g., associated with an exercise category and/or one or more sub-categories) based on any suitable combination of information known about the user (e.g., exercise information, user-profile information, vital sign information, collectively referred to herein as "fitness-related information"). As a non-limiting example, an exercise category/sub-category may be determined for the user by comparing fitness-related information associated with the user to fitness-related information associated with other known users. Once the user is associated with one or more exercise categories/sub-categories, a customized exercise-related recommendation may be identified and provided to the user. The exercise-related recommendation provided may be identified by matching, or determining a relationship between an exercise category/sub-category of the user and an exercise category/sub-category associated with a previously-stored exercise-related recommendation. Accordingly, the system may utilize fitness-related information associated with other user's, and classifications associated with such users, to classify a known/unknown user in order to identify particular recommendations that may be applicable to that user.

In some embodiments, a classification model for classifying a user and/or input data (e.g., fitness-related information) associated with a user may be generated and maintained. A "classification model" can refer to a machine-learning technique that classifies input data based on a training set of historical data for which category membership is known. A classification model may utilize any suitable supervised machine-learning techniques, such as logistic regression algorithms, to assign a real-value output (e.g., one or more exercise categories and/or sub-categories) to each input (e.g., fitness-related information associated with a user). The system may be configured to maintain training data such as historical fitness-related information for which classifications (e.g., exercise categories and/or sub-categories) are known. Such classifications, in some cases, may be assigned manually and stored as an association with the fitness-related information to which the classification pertains.

In at least one embodiment, a classification model may utilize any suitable unsupervised machine-learning techniques, such as cluster analysis algorithms (e.g., k-means, etc.), to identify users that are similar to one another. Execution of a cluster analysis algorithm may cause a set of objects (e.g., users, fitness-related information) to be grouped in a way that objects of the same group (called a "cluster") are more similar to each other than users of other groups (clusters). In a non-limiting example, cluster analysis may be utilized to classify previously unclassified historical data, where user/fitness-related information is clustered into a suitable number of clusters and each cluster is assigned a classification. The assigned classifications may be then utilized as training data to train a classification model with a supervised machine-learning algorithm. Subsequent fitness-related information may be added to the training data set, and the classification model may be retrained on the new training data set at any suitable time.

In at least one embodiment, expected progress data may be maintained by the system and utilized to provide customized exercise-related recommendations. Expected progress data may identify any suitable number of classification categories (e.g., one or more exercise categories) and/or sub-categories (e.g., one or more exercise levels). By way of example, an exercise category might indicate that a user is an amateur weight-lifter, an elderly person, an adolescent, an advanced runner, and/or an overweight person, to name a few. It should be appreciated that exercise categories/sub-categories may vary, and that particular exercise categories/sub-categories would be identifiable to one skilled in the art. In some embodiments, the user may be associated with more than one exercise category. Additionally, the user may be associated with one or more sub-categories. By way of example, an "amatuer weight-lifter" exercise category may be associated with a sub-category (e.g., level 1, level 2, level 3, etc.) of a classification category. In some cases, these sub-categories may be distinct from one another such that a user may be associated with only one sub-category at a time.

In some embodiments, expected progress data may define relationships between categories, between sub-categories, and/or between categories and sub-categories. Expected progress data may further be associated with one or more fitness goals. For example, expected progress data may define a progress path that defines a progression/sequence of categories and/or sub-categories by which a user should progress. In some embodiments, a progress path may specify a time period associated with each category/sub-category in the progress path (e.g., 2 weeks for level 1, 3 weeks for level 3, etc.) or a time period associated with the entire progress path (e.g., 2 months from setting a goal to achieving the goal).

By way of example, a user may be classified as a level 1, amateur weight lifter. A level 1, amateur weight lifter, may be used to classify a person who meets certain characteristics associated with the amateur weight-lifter category and the level 1 sub-category of the amateur weight-lifter category. For example, a person classified as a level 1, amateur weight lifter, may be associated with user-profile information indicating a fitness goal related to weight lifting. The person may be associated with exercise information that indicates that the user can lift up to a weight amount (e.g., 5 lbs. or less), up to a particular number of lifts in one set (e.g., at most 10 lifts, 5 lifts, etc.), and can repeat a set up to a particular number of sets (e.g., groups of lifts), or any suitable combination of the above. In some examples, the expected progress data may identify a progress path for the user to reach a category and/or sub-category associated with a particular goal, or a progress path that identifies a particular degree of improvement (e.g., an increase in level and/or category over a particular period of time). It should be appreciated that a fitness goal need not be identified by the user, in some embodiments, a progress path may be identified that generally progresses the user toward better health/fitness with respect to one or more characteristics (e.g., user weight, stamina, strength, oxygen level, blood pressure level, sleep patterns, dietary changes, unhealthy vices (e.g., smoking), etc.).

Recommendations may be identified and provided to a user (e.g., presented on a user device or the exercise machine) according to the user's exercise category/sub-category and a category/sub-category of individual recommendations. In some cases, the particular recommendation identified may be associated with a category/sub-category identified in the progress data as being appropriate for a user associated with a particular exercise category/sub-category.

In at least one embodiment, a database of recommendations (e.g., exercise-related recommendations) may be maintained. In some examples, recommendations may be manually generated and stored. Additionally, or alternatively, recommendations may be generated according to expected progress data. As described above, an exercise-related recommendation can at least indicate to a user a change in a type of exercise machine utilized by a user and/or the manner in which a user utilizes a particular exercise machine. By way of example, a recommendation may suggest that the user increase or decrease speed on the currently utilized exercise machine. Another recommendation may suggest that the user utilize a different exercise machine than the one currently being utilized. Yet, another recommendation may suggest that the user increase or decrease weight and/or repetitions. The content of the recommendations provided may be ascertained by one skilled in the art. In some embodiments, recommendations may be associated with a category, a sub-category, a fitness goal, or any suitable combination of the above.

In some embodiments, progress of the user and/or effectiveness of a provided recommendation may be tracked. Once a user is provided a customized exercise-related recommendation, the user's fitness-related information (e.g., exercise information, user-profile information, and vital sign information) may be tracked to determine whether the user performed an action associated with the provided recommendation. By way of example, if the user is provided a customized exercise-related recommendation that suggests increasing the speed on a treadmill, the exercise information associated with the user (e.g., collected by sensors attached to the treadmill) may be analyzed to determine that the user did (or did not) increase the speed of the treadmill as suggested. Depending on whether the user performed the action suggested, then subsequent exercise information may be analyzed and attributed to the provided recommendation. In some cases, exercise information may only be attributed to a provided recommendation if the user is identified as having performed the suggested action.

In some embodiments, the system may analyze subsequent fitness-related information associated with the user (e.g., fitness-related information attributed to a recommendation), to determine that the recommendation resulted in the user progressing within some threshold of a determined progress path or, in some cases, toward a fitness goal in general. By way of example, according to an identified progress path associated with the user, the user is supposed to be able to run at a particular speed (e.g., 3.5 miles per hour) for a particular duration (e.g., 30 minutes), within the next month, the user's exercise information may be tracked to determine that the user is progressing toward that ability according to the determined progress path. Based on a determination that the user is progressing in according with the identified progress path, the system may identify the recommendation as being one that has been effective. In some embodiments, the recommendation may be assigned a label, a score, or the like, that indicates a degree of effectiveness. Accordingly, when providing recommendations to other users, recommendation scores/labels may be utilized to identify effective (or the most-effective) recommendation(s) for those users.

FIG. 1 is a simplified block diagram illustrating an example flow 100 for providing a customized exercise-related recommendation (e.g., customized exercise-related recommendation 102), according to at least one embodiment. At 104, exercise information may be collected for a group of users (e.g., users 106). In some examples, the exercise information collected for the users 106 may be stored in exercise information data store 108, a data store configured to store such information. The exercise information collected at 104 may include any suitable information collected by a sensor attached to an exercise machine, a user device, or the like. An exercise machine may include any fitness-related machine such as, but not limited to, treadmill machines, elliptical machines, weight-training machines, rowing machines, stationary bicycles, or any suitable object (electrically-powered or otherwise) that may be utilized by a user for exercise purposes. Exercise machine 110 (e.g., depicting a stationary bicycle) is an example of an exercise machine.

At 112, it may be identified that a user (e.g., user 114) of the group is interacting with exercise machine 110. In some embodiments, the exercise machine 110 may be attached to one or more sensors (e.g., an accelerometer, a gyroscope, a heart rate monitor, an oxygen sensor, etc.) such as sensor 116. Sensor 116, or any sensor attached to the exercise machine 110 may be utilized to identify when a user is interacting with the machine. In some embodiments, the sensor 116 may be configured to transmit and receive information via any suitable network according to any suitable communications protocol. By way of example, the sensor 116 may be configured to communicate via the Internet, via a Bluetooth (low-energy) protocol, via a text messaging protocol, or the like.

In at least one embodiment, the exercise machine 110 may be configured with an input device (e.g., a touch pad, a keyboard, a mouse, etc.) that may be utilized by the user to input identification information (e.g., a username or other suitable user identifier) at the exercise machine 110. In other embodiments, the user may carry a user device (e.g., a cell phone, a fitness watch, etc.), such as user device 118, that may be configured to communicate with the exercise machine 110 (or a sensor attached to the exercise machine 110). Communications between the exercise machine 110 and the user device 118 may enable identification between the two devices. Accordingly, the exercise machine 110 may provide a machine identifier to the user device 118 and/or the user device 118 may provide a user identifier and/or device identifier to the exercise machine 110.

In some embodiments, identifying that the user 114 is interacting with the exercise machine 110 may include identifying that a device associated with the user 114 is within a threshold distance (or shortest distance with respect to other devices of other users) to the exercise machine 112 while the exercise machine 110 is in use. In some embodiments, identifying that the user 114 is interacting with the exercise machine 112 may include determining that a user identifier has been entered at an input device of the exercise machine 112. In still further embodiments, identifying that the user 114 is interacting with the exercise machine 112 may include identifying that a device associated with the user 114 is within a threshold distance of the exercise machine 110 over a threshold period of time.

At 120, a customized exercise-related recommendation may be generated for the user 114 based on the collected exercise information associated with the users 106. By way of example, the system may determine that the user 114 is similar in some respect to the users 106 (or some subset of the users 106). In some embodiments, recommendations provided to the users 106 may be identified. Additionally, or alternatively, recommendations associated with an exercise category and/or sub-category corresponding to the user 114 (and users 106) may be identified.

At 122, the customized exercise-related recommendation 102 may be provided to the user 114 (e.g., via a component of the user device 118, via a component of the exercise machine 110, etc.). In some embodiments, the customized exercise-related recommendation 102 may be selected from the identified recommendations associated with the users 106 and/or a category associated with the users 106. The customized exercise-related recommendation 102 may be selected from the identified recommendations according to a recommendation score (indicating a degree of effectiveness associated with the recommendation) and/or based on exercise information and/or user profile information associated with the user 114.

Figure 2:
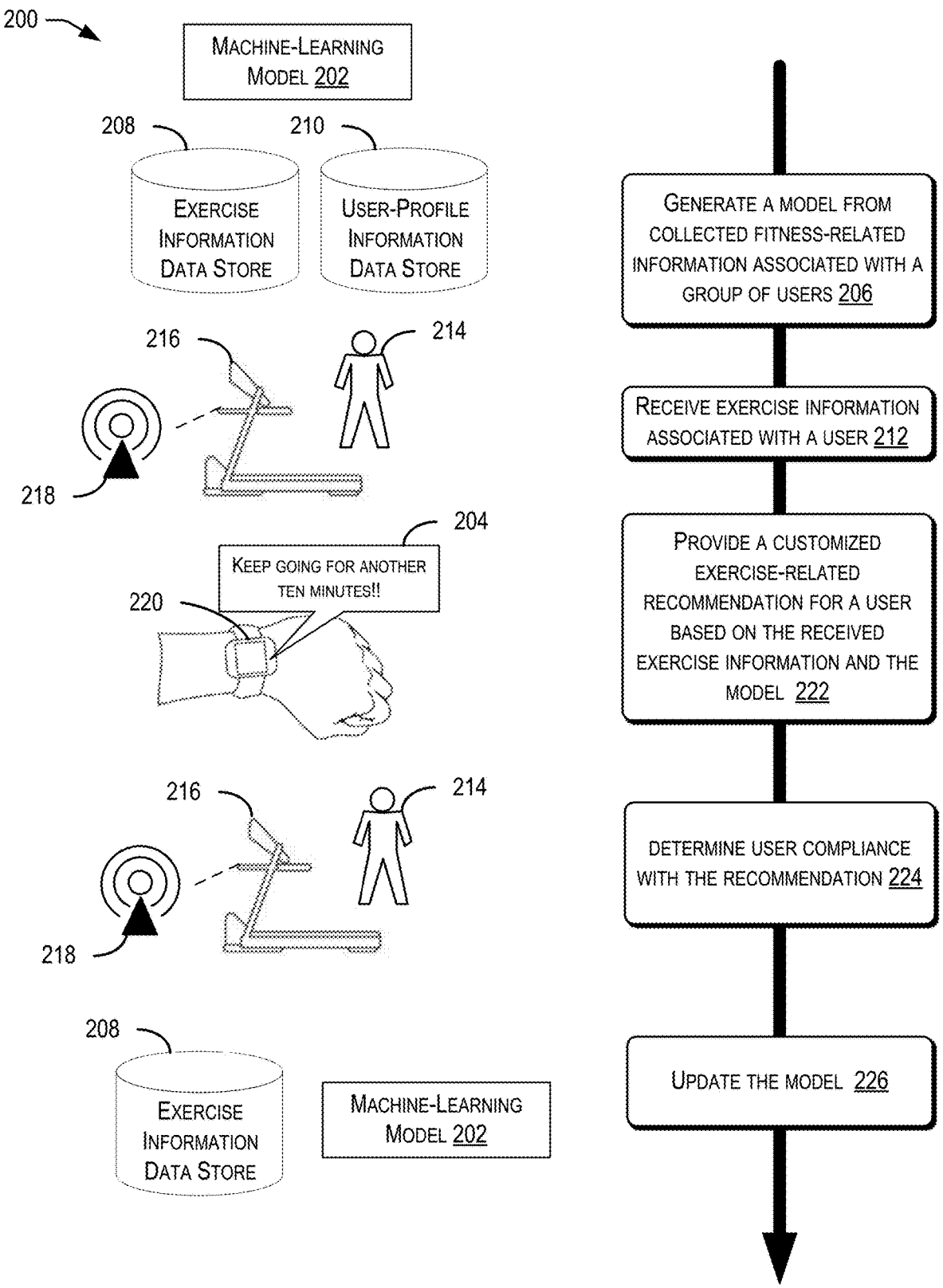
FIG. 2 is a simplified block diagram illustrating an example flow for maintaining a machine-learning model utilized to provide customized exercise-related recommendations, according to at least one embodiment.

FIG. 2 is a simplified block diagram illustrating an example flow 200 for maintaining a machine-learning model 202 utilized to provide customized exercise-related recommendations (e.g., customized exercise-related recommendation 204), according to at least one embodiment. At 206, a model (e.g., the machine-learning model 202, an example of a classification model) may be generated from collected fitness-related information associated with a group of users (e.g., the users 106 of FIG. 1). The collected information may include any suitable combination of fitness-related information (e.g., exercise information, vital sign information, and/or user-profile information) associated with the users 106. In some embodiments, the collected exercise information associated with the users 106 may be stored in exercise information data store 208 (e.g., the exercise information data store 108 of FIG. 1), a data store configured to store such information. Similarly, collected vital sign information and/or user-profile information associated with the users 106 may be stored in the user-profile information data store 210, perhaps within a user profile record. In some cases, all fitness-related information, including exercise information, may be stored in the user profile within the user-profile information data store 210.

In some embodiments, the machine-learning model 202 may be utilized to classify a user (e.g., the user 214) as being associated with a particular exercise category. The machine-learning model 202 may be generated to classify input data (the received fitness-related information, such as exercise information) based on a training set of historical data (historical fitness-related information of the users 106) for which category membership is known.

At 212, exercise information may be associated with a user 214 may be received (e.g., from exercise machine 216). The exercise information received at 212 may include any suitable exercise information collected by a sensor 218 attached to an exercise machine 216, a user device (e.g., the user device 220), or the like. Although depicted as a treadmill, the exercise machine 216 may include any fitness-related machine such as, but not limited to, treadmill machines, elliptical machines, weight-training machines, rowing machines, stationary bicycles, or any suitable machine (electrically-powered or otherwise) that may be utilized by a user for exercise purposes.

At 222, the customized exercise-related recommendation 204 may be provided to the user 214 (e.g., via the user device 220). In some embodiments, the customized exercise-related recommendation 204 may be identified utilizing the machine-learning model 202 and the exercise information received at 212. By way of example, the exercise information received at 212 may be utilized as input data for the machine-learning model 202. The machine-learning model 202 may be configured to classify the exercise information as belonging to a particular exercise category. The user 214 may then be associated with the exercise category. Candidate recommendations associated with the same exercise category as the input data may be identified and the customized exercise-related recommendation 204 may be selected from the identified candidate recommendations.

At 224, user compliance with the customized exercise-related recommendation may be determined. By way of example, subsequent exercise information associated with the user 214 may be received. The subsequent exercise information may be related to the exercise machine 216, or the subsequent exercise information may be related to a different exercise machine. The subsequent exercise information may be analyzed to determine whether the user 214 complied with the customized exercise-related recommendation 204. If the determination is made that the user 214 did comply with the customized exercise-related recommendation 204, a score associated with the customized exercise-related recommendation 204 may be adjusted (e.g., increased to indicate that the customized exercise-related recommendation 204 has been effective in at least one use case). In some embodiments, the subsequent exercise information may be stored in the exercise information data store 208.

At 226, the machine-learning model 202 may be updated. In some embodiments, the collected fitness-related information (e.g., the exercise information contained in the exercise information data store 208 and/or the vital sign/user-profile information contained in the user-profile information data store 210) may be utilized to retrain the machine-learning model 202 in order to improve the model's accuracy in classifying future users and/or fitness-related information.

Figure 3:
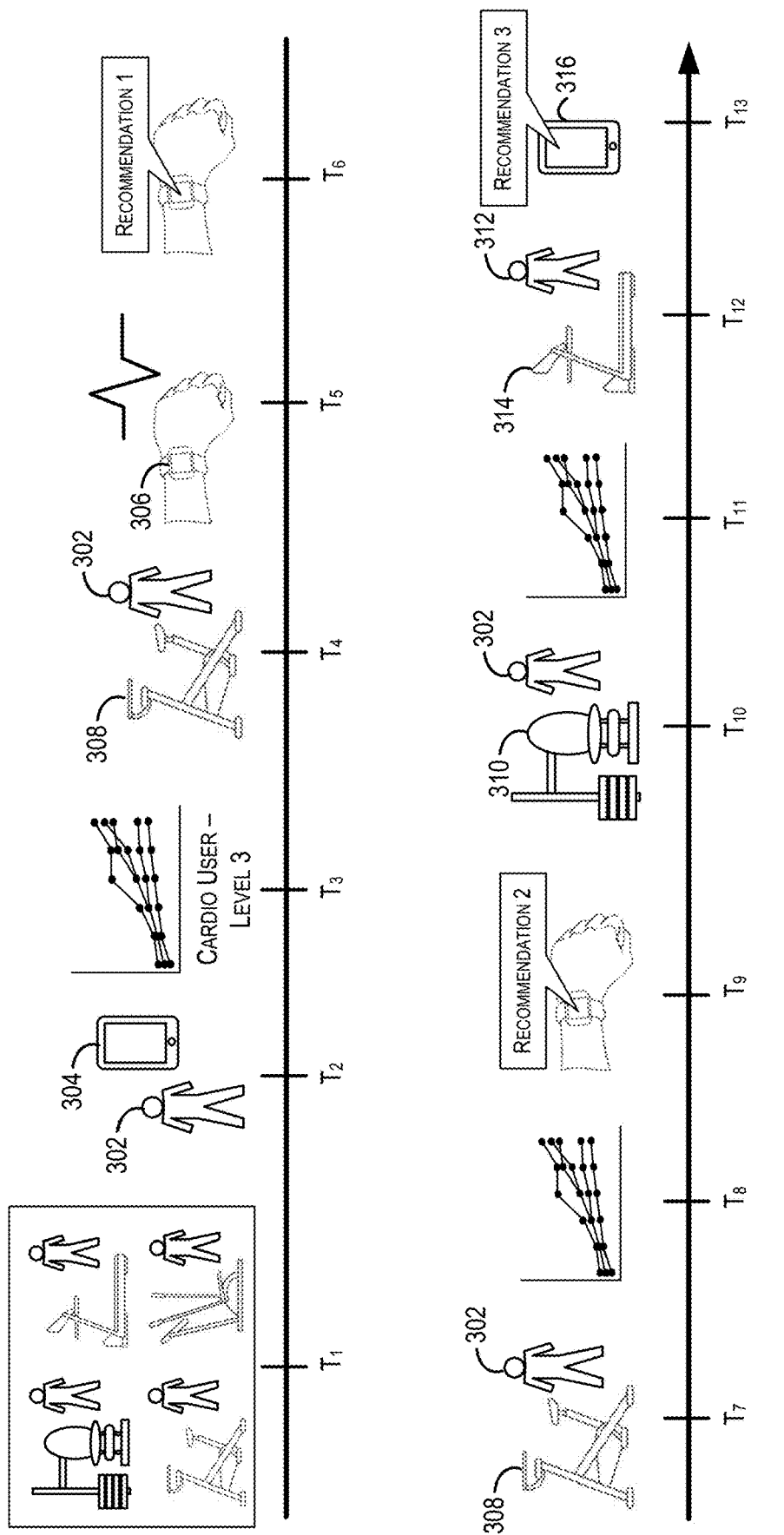
FIG. 3 is a simplified block diagram illustrating an example flow for providing a number of customized exercise-related recommendations, according to at least one embodiment.

FIG. 3 is a simplified block diagram illustrating an example flow 300 for providing a number of customized exercise-related recommendations (e.g., the customized exercise-related recommendation 102 of FIG. 1 and/or the customized exercise-related recommendation 204 of FIG. 2), according to at least one embodiment. It should be appreciated that the flow 300 is intended for illustrative purposes only and is not intended to limit the scope of this disclosure. Although a particular number of events are depicted in FIG. 3, any suitable number of events may occur. Additionally, any suitable combination of the events depicted in FIG. 3, or some combination of different events, may be utilized in any example discussed herein. The order of the events described below may occur in any suitable order, although not necessarily at the times and/or in the order depicted. In the example of FIG. 3, the times $T_1$-$T_{13}$ are intended to times that occur in sequential order where time $T_2$ occurs after time $T_1$, time $T_3$ occurs after time $T_2$, and so on.

At time $T_1$, fitness-related information (e.g., exercise information, vital sign information, user-profile information, etc.) may be collected for a group of users (e.g., the users 106 or a different set of users). The fitness-related information may be associated with any suitable number and/or types of exercise machines (e.g., the exercise machine 110 of FIG. 1 and/or the exercise machine 216 of FIG. 2).

At time $T_2$, a user (e.g., the user 302) may register user-profile information with the system as part of a registration process provided by the exercise recommendation engine discussed herein. In some embodiments, the user-profile information may be entered by the user 302 utilizing a user device 304. The user device 304 may be configured to execute or otherwise manage applications and/or instructions for collecting and displaying user-profile information, vital sign information, exercise information, or any suitable information associated with the user. The user device 304 may receive inputs from a user at a user interface provided at a component of the user device 304 (e.g., a touch display, a microphone, a mouse, or any suitable input/output (I/O) device in communication with the user device 304). Likewise, outputs (e.g., customized exercise-related recommendations, feedback information, exercise information, user-profile information, vital sign information, etc.) may be provided to the user via the user device 304 (e.g., on a display, audibly, via haptic feedback (e.g., vibration), etc.).

At time $T_3$, the user 302 and/or the user-profile information associated with the user 302 may be classified utilizing a previously generated classification model (e.g., the machine-learning model 202 of FIG. 2). By way of example, the user-profile information provided by the user 302 at time Ta may be utilized as input data in the previously generated classification model in order to identify a particular category (e.g., an exercise category such as "cardio user") for the user and/or input data. In some examples, the previously generated classification model may be configured (e.g., trained utilizing historical user-profile information associated with other users and/or exercise information associated with other users) to identify one or more sub-categories (e.g., level 1, level 2, "amateur," "intermediate," etc.) for the user-profile information. By way of example only, the user 302 may provide user-profile information that indicates that the user has self-identified that he is capable of running, at most, 1 minute, at a speed of 1 mile per hour. The previously generated classification model may utilize such information as input to classify the user and/or the user-profile information as being indicative of a particular exercise category (e.g., cardio user), and in some cases, a particular sub-category (e.g., level 3).

At time $T_4$, the user 302 may interact with an exercise machine (e.g., the exercise machine 308). The interaction may be detected by the system based on a distance between the user device 304 (or another user device such as user device 306, a body-worn device) and the exercise machine 308. In some embodiments, the user device 304 and/or the user device 306 may exchange and/or provide identification information (e.g., device identification information) with the exercise machine 308. Additionally, or alternatively, the user device 304 and/or the user device 306 may provide user identification information (e.g., a username, a name, or any suitable user identifier) to the exercise machine 308. In at least one embodiment, the user device 304/306 and/or the exercise machine 308 may be configured to provide received identification information (e.g., device and/or user) to the exercise recommendation engine described herein. Received user and/or device identification information may be utilized to determine that the user 302 is interacting with the exercise machine 308.

In at least one embodiment, determining that the user 302 is interacting with the exercise machine 308 may include determining that the user device 304/306 is within a threshold distance (or shortest distance with respect to other devices of other users) to the exercise machine 308 while the exercise machine 308 is in use. In some embodiments, determining that the user 302 is interacting with the exercise machine 308 may include determining that a motion of the user device 304/306 is similar (within a threshold degree of similarity) to a motion that would be required to operate the exercise machine 308, or a motion that is currently being performed with the exercise machine 308. In some embodiments, identifying that the user 302 is interacting with the exercise machine 308 may include determining that a user identifier has been entered at an input device of the exercise machine 308. In still further embodiments, identifying that the user 302 is interacting with the exercise machine 308 may include identifying that a device associated with the user 302 (e.g., the user device 304 and/or the user device 306) is within a threshold distance of the exercise machine 308 over a threshold time period.

At time $T_5$, fitness-related information may be received. In some examples, the fitness-related information may include vital sign information (e.g., heart rate information, an oxygen level, blood pressure, or any suitable sensor data such as data collected by a camera, a heart-rate monitor, an oxygen sensor, a blood pressure sensor, etc.) and/or exercise information associated with the user 302 (or associated with a user profile of the user 302). In some embodiments, the vital sign information may be collected and transmitted by the user device 306. Additionally, or alternatively, vital sign information may be collected and transmitted by the exercise machine 308. Still further, exercise information for the user 302 may be collected and transmitted by the exercise machine 308 and/or the user device 306.

In at least one example, the fitness-related information (vital sign information and/or exercise information) received may be utilized as input to the machine-learning model in order to provide further input with which to classify the user 302. By way of example, although the user was associated at time $T_3$ with the exercise category "cardio user" and sub-category "level 3", the vital sign information (e.g., received from the user device 306), in conjunction with the exercise information (e.g., received from the exercise machine 308) may indicate that the user is out of breath and/or his heart-rate is over a threshold value given particular characteristics of the exercise information (e.g., indicating that the user is peddling the exercise machine 308 at a certain speed, given a particular resistance). It may be the case, that level 3 users, do not typically exhibit such vital sign information given the exercise being performed. Accordingly, the exercise category and/or sub-category of the user may be adjusted depending on the output provided by the machine-learning model. By way of example, the output provided by the machine-learning model may indicate that the user should be associated instead with an exercise category of "cardio user" with a sub-category of "level 1." Level 1, in this context, may indicate a set and/or degree of capabilities related to cardio-based exercises that may be different from a set and/or degree of capabilities related to cardio-based exercises that a level 3 user may be capable of performing.

At time $T_6$, a customized exercise-related recommendation (e.g., recommendation 1) may be provided to the user 302. In some examples, recommendation 1 may be provided to the user 302 via a user device (e.g., the user device 304 and/or the user device 306) via any suitable method for electronic communication (e.g., push notification, email, text, audio alert, textual output, etc.).

In some embodiments, expected progress data may be utilized to identify recommendation 1 from a set of candidate recommendations. The expected progress data may identify protocol sets (e.g., rules) that define relationships between any suitable combination of categories and/or sub-categories. By way of example, the expected progress data may determine a progress path for the user 302 (associated with the exercise category "cardio user," and sub-category "level 1"). By way of example, a progress path may be determined for the user 302 may identifying that the user 302 has user-profile information indicating that the user has a particular cardiovascular-related goal. For purposes of this example, the cardiovascular goal could indicate that the user eventually desires to be able to run 1 mile in under 6 minutes. The cardiovascular goal may correspond to an exercise category (e.g., "cardio user") and a sub-category (e.g., level 10). Accordingly, the expected progress data may be utilized to identify a progress path (e.g., a sequence of sub-categories and/or categories) that indicate a progression that the user 302 may achieve that may eventually result in achieving his cardiovascular goal.

It should be appreciated that a fitness goal need not be a factor for identifying a progress path. That is, in some embodiments, a progress path may be identified that generally progresses the user toward better health/fitness with respect to one or more characteristics (e.g., user weight, stamina, strength, oxygen level, blood pressure level, sleep patterns, dietary changes, unhealthy vices (e.g., smoking), etc.) rather than to a particular fitness goal.

It should be appreciated that in some embodiments, a progress path for the user 302 may identify a particular degree of improvement (e.g., an increase in level and/or category over a particular time period). For example, a progress path may indicate that the user 302 should be associated with a next sub-category within a week, month, year, or any suitable time period.

In at least one embodiment, the recommendation 1 may be one of a set of candidate recommendations maintained as part of a database of recommendations (e.g., exercise-related recommendations). As described above, a recommendation can indicate to the user 302 a change in a type of exercise machine utilized by a user and/or the manner in which a user utilizes a particular exercise machine. By way of example, recommendation 1 may suggest that the user 302 increase a speed of the exercise machine 308. Another recommendation may suggest that the user utilize a different exercise machine than the one currently being utilized. In still further examples, recommendation 1 may suggest that the user continue with the exercise currently being performed for an additional time period (e.g., ten minutes).

In at least one embodiment, recommendation 1 (and each of the recommendations described herein) may be associated with a category (e.g., an exercise category), a sub-category (e.g., beginning, intermediate, advanced, expert, etc.), and/or a fitness goal. Thus, in some embodiments, recommendation 1 may be identified for the user 2 based determining that the progress path indicates that the user should be provided recommendations associated with a particular category and/or sub-category. The category and/or sub-category of recommendation 1 may be the same or different from a category and/or sub-category with the user 302 is currently associated.

At time $T_7$, additional fitness-related information (e.g., vital sign information, user-profile information, and/or exercise information associated with the user 302) may be received. Time $T_5$ and $T_7$ may occur within a same exercise session (e.g., a workout session) or time $T_7$ may occur during a subsequent exercise session of the user 302. The additional fitness-related information may be utilized as input to the machine-learning model in order to provide further input with which to classify the user 302. At time $T_8$, an exercise category and/or sub-category may be adjusted or maintained based on the information received at $T_7$. In some embodiments, progress data may be adjusted in response to determining that the fitness-related information (and/or other collected fitness-related information) indicates that the progress data (or progress paths determined from the progress data) defines progressions that a relatively small number and/or percentage of users are able to maintain. Accordingly, by tracking and analyzing fitness-related information over time, the system may adjust progress data such that progress paths may be provided that more realistically define an expected progression.

At time $T_9$, the recommendation 2 (e.g., one of a set of candidate recommendations maintained as part of a database of recommendations) may be provided to the user 302 (e.g., via the user device 306). Recommendation 2 may suggest that the user 302 increase a resistance associated with the exercise machine 308. In some embodiments, the user 302 may accept the recommendation and manually modify settings of the exercise machine 308. In other examples, acceptance of the recommendation 2 may be indicated via the user device 306 and the setting of the exercise machine 308 may be automatically updated (e.g., by transmitting updated setting information (e.g., speed, incline, resistance, weight, to the exercise machine 308). Additionally, or alternatively, recommendation 2 may suggest that the user utilize a different exercise machine than the one currently being utilized such as exercise machine 310. In still further examples, recommendation 2 may suggest that the user continue with the exercise currently being performed for an additional time period (e.g., ten minutes).

At time $T_{10}$, the user 302 may interact with an exercise machine 310. The interaction may be detected by the system in a similar manner as suggested above. Fitness-related information corresponding to the user 302 and/or the exercise machine 310 may be received. The fitness-related information may be utilized as input to the machine-learning model in order to provide further input with which to classify the user 302. At time $T_{11}$, an exercise category and/or sub-category may be adjusted or maintained based on the information received at $T_{10}$. It should be appreciated that any of suitable information received above may be utilized to update (e.g., retrain) the machine-learning model.

At time $T_{12}$, the user 312 may interact with an exercise machine (e.g., the exercise machine 314). The interaction may be detected by the system in a similar manner as suggested above with respect to detecting interactions between a user and an exercise machine. Fitness-related information corresponding to the user 312 and/or the exercise machine 314 may be received. Such information may be utilized as input to the updated machine-learning model in order to provide input with which to classify the user 312. Accordingly, the fitness-related information associated with the user 302 may be utilized by the machine-learning model to classify the user 312.

At time $T_{13}$, the user 312 may be provided recommendation 3 via a user device associated with the user 312 (e.g., user device 316). Recommendation 3 may be identified in a similar manner, utilizing similar techniques, as identified above with respect to identifying recommendations for user 302.

Figure 4:
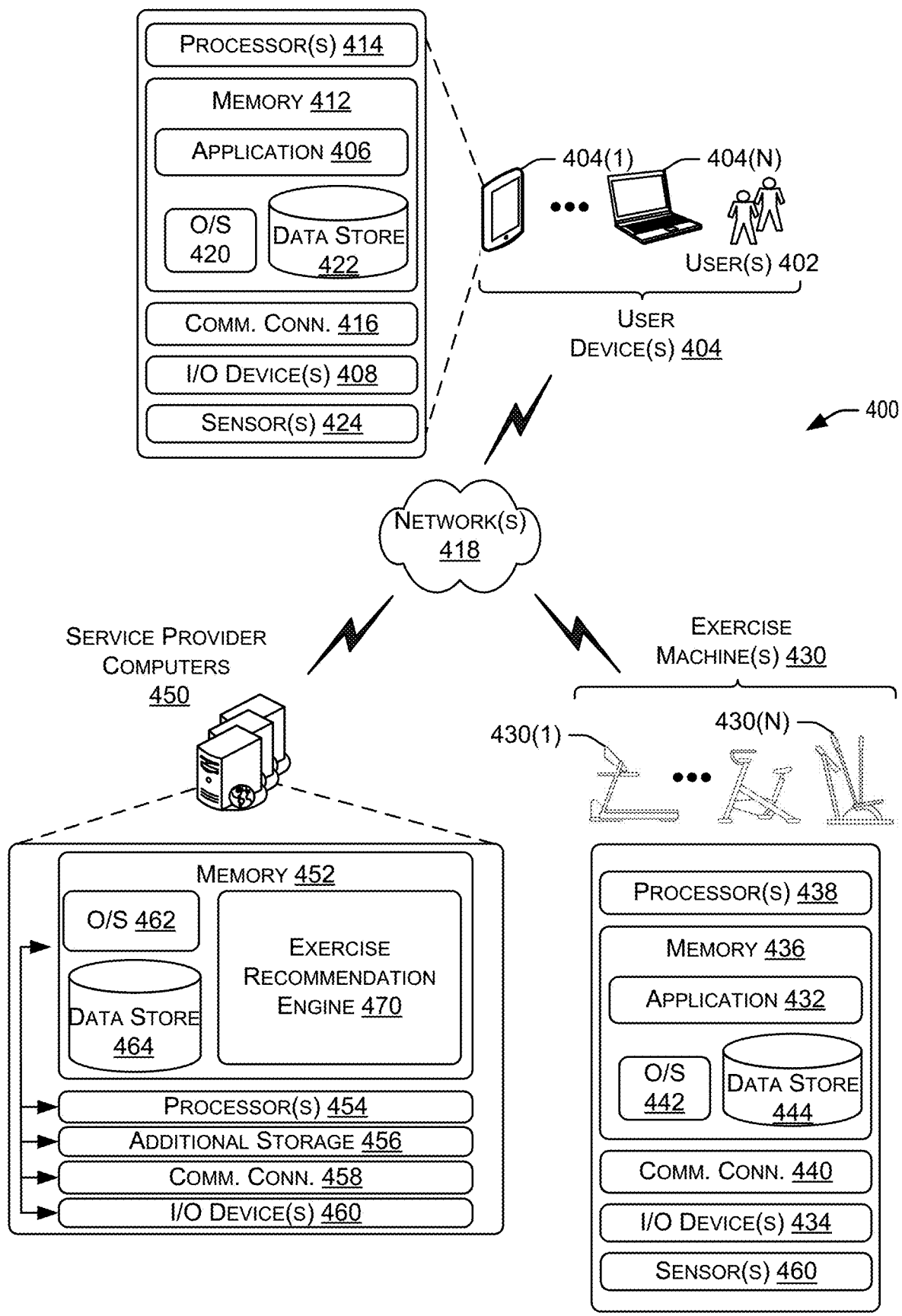
FIG. 4 is a simplified block diagram illustrating an example system for implementing an exercise recommendation engine, according to at least one embodiment.

FIG. 4 is a simplified block diagram illustrating an example system 400 for implementing an exercise recommendation engine 470, according to at least one embodiment. It should be appreciated that the exercise recommendation engine 470 may include executable code to cause a processor to implement any of examples discussed herein. In some examples, user device(s) 404(1)-404(N) (e.g., the user device 118, 220, 304, 306, and 316), collectively referred to as the user device(s) 404, may individually be configured to execute or otherwise manage applications (e.g., the application 406) or instructions for collecting and/or presenting information. The user device(s) 404 may collect inputs from a user at a user interface (e.g., via I/O device(s) 408). The user device(s) 404 may further provide outputs via such user interfaces. I/O device(s) 408 may include, but are not limited to, a touch input device, a keyboard, a mouse, a pen, a voice input device, a display, a speaker, a printer, etc.

The user device(s) 404 may be any type of computing device such as, but not limited to, a mobile phone (e.g., a smartphone), a tablet computer, a personal digital assistant (PDA), a laptop computer, a desktop computer, a thin-client device, a smart watch, a wireless headset, or the like. In one illustrative configuration, the user device(s) 404 may include at least one memory 412 and one or more processing units (or processor(s)) 414. The processor(s) 414 may be implemented as appropriate in hardware, computer-executable instructions, or combinations thereof. Computer-executable instruction or firmware implementations of the processor(s) 414 may include computer-executable or machine-executable instructions written in any suitable programming language to perform the various functions described.

The memory 412 may store program instructions that are loadable and executable on the processor(s) 414, as well as data generated during the execution of these programs. Depending on the configuration and type of the user device(s) 404, the memory 412 may be volatile (such as random access memory (RAM)) and/or non-volatile (such as read-only memory (ROM), flash memory, etc.). In some implementations, the memory 412 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 412 may be an example of a non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 412 may be an example of non-transitory computer storage media. Additional types of computer storage media that may be present in the user device(s) 404 may include, but are not limited to, phase-change RAM (PRAM), SRAM, DRAM, RAM, ROM, electrically erasable programmable read-only memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device(s) 404. Combinations of any of the above should also be included within the scope of non-transitory computer-readable storage media.

Alternatively, computer-readable communication media may include computer-readable instructions, program modules, or other data transmitted within a data signal, such as a carrier wave, or other transmission. However, as used herein, computer-readable storage media does not include computer-readable communication media.

The user device(s) 404 may also contain communications connection(s) 416 that allow the user device(s) 404 to communicate with a data store, another computing device or server, user terminals and/or other devices via one or more networks (e.g., network(s) 418). Network(s) 418 may include any one or a combination of many different types of networks, such as cable networks, the Internet, wireless networks, cellular networks, satellite networks, other private and/or public networks, or any combination thereof.

Turning to the contents of the memory 412 in more detail, the memory 412 may include an operating system 420 and/or one or more application programs or services for implementing the features disclosed herein. The memory 412 may also be configured to store data (e.g., user-profile information) within data store 422. The user device(s) 404 can perform all of the operations described herein, or the user device(s) 404 can perform at least some of the operations described herein.

In at least one embodiment, the user device(s) 404 may contain one or more sensor(s) 424. The sensor(s) 424 may be configured to collect any suitable sensor data indicating any suitable metric including, but not limited to, motion data for the user device(s) 404, vital sign information of the user, or the like). The sensor(s) 446 may be any type of sensing device such as, but not limited to, an accelerometer, a gyroscope, a camera (or other image-capturing device), a sensor configured to collect vital sign information (e.g., a heart-rate monitor, an oxygen monitor, a blood pressure monitor, etc.), or the like.

In some examples, exercise machines 430(1)-430(N) (e.g., the exercise machine 110, 216, 308, 310, and 314), collectively referred to as the exercise machine(s) 430, may individually be configured to execute or otherwise manage applications (e.g., the application 432) or instructions for collecting and/or presenting information. The exercise machine(s) 430 may collect inputs from a user at a user interface (e.g., via I/O device(s) 434). The exercise machine(s) 430 may further provide outputs via such user interfaces. I/O device(s) 434 may include, but are not limited to, a touch input device, a keyboard, a mouse, a pen, a voice input device, a display, a speaker, a printer, etc.

The exercise machine(s) 430 may be any type of exercise machine such as, but not limited to, a treadmill, an elliptical, a stationary bicycle, a weight-lifting machine, a step machine, a rowing machine, or the like. In one illustrative configuration, the exercise machine(s) 430 may include at least one memory 436 and one or more processing units (or processor(s)) 438. The processor(s) 438 may be implemented as appropriate in hardware, computer-executable instructions, or combinations thereof. Computer-executable instruction or firmware implementations of the processor(s) 438 may include computer-executable or machine-executable instructions written in any suitable programming language to perform the various functions described.

The memory 436 may store program instructions that are loadable and executable on the processor(s) 438, as well as data generated during the execution of these programs. Depending on the configuration and type of the exercise machine(s) 430, the memory 436 may be volatile (such as random access memory (RAM)) and/or non-volatile (such as read-only memory (ROM), flash memory, etc.). In some implementations, the memory 436 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 436 may be an example of a non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 436 may be an example of non-transitory computer storage media. Additional types of computer storage media that may be present in the exercise machine(s) 430 may include, but are not limited to, phase-change RAM (PRAM), SRAM, DRAM, RAM, ROM, electrically erasable programmable read-only memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the exercise machine(s) 430. Combinations of any of the above should also be included within the scope of non-transitory computer-readable storage media.

Alternatively, computer-readable communication media may include computer-readable instructions, program modules, or other data transmitted within a data signal, such as a carrier wave, or other transmission. However, as used herein, computer-readable storage media does not include computer-readable communication media.

The exercise machine(s) 430 may also contain communications connection(s) 440 that allow the exercise machine(s) 430 to communicate with a data store, another computing device or server, user terminals and/or other devices via network(s) 418.

Turning to the contents of the memory 436 in more detail, the memory 436 may include an operating system 442 and/or one or more application programs or services for implementing the features disclosed herein. The memory 436 may also be configured to store data (e.g., user-profile information) within data store 444. The exercise machine(s) 430 can perform all of the operations described herein, or the exercise machine(s) 430 can perform at least some of the operations described herein.

In at least one embodiment, the exercise machine(s) 430 may contain one or more sensor(s) 446. The sensor(s) 446 may be configured to collect any suitable sensor data including, but not limited to, exercise information associated with the exercise machine(s) 430 (e.g., any suitable metric such as a speed, an amount of weight being lifted, a range of motion associated with a part of an exercise machine, vital sign information of the user, a number of repititions performed, and the like). The sensor(s) 446 may be any type of sensing device such as, but not limited to, an accelerometer, a gyroscope, a camera (or other image-capturing device), a sensor configured to collect vital sign information (e.g., a heart-rate monitor, an oxygen monitor, a blood pressure monitor, etc.), or the like.

The service provider computers 450, perhaps arranged in a cluster of servers or as a server farm, may host the application 406 and/or the application 432 operating on the user device(s) 404 or the exercise machine(s) 430, respectively. Additionally, or alternatively, the service provider computers 450 may host cloud-based software services. Other server architectures may also be used to host the application 406, the application 432, and/or cloud-based software services.

In some aspects, the service provider computers 450 may also be any suitable type of computing devices such as, but not limited to, a mobile phone, a smart phone, a personal digital assistant (PDA), a laptop computer, a desktop computer, a server computer, a thin-client device, a tablet PC, etc. Additionally, it should be noted that in some embodiments, the service provider computers 450 are executed as part of a cloud-computing environment. In some examples, the service provider computers 450 may be in communication with the user device(s) 404 and/or the exercise machine(s) 430 via the network(s) 418 or via other network connections.

In one illustrative configuration, the service provider computers 450 may include at least one memory 452 and one or more processing units (or processor(s)) 454. The processor(s) 454 may be implemented as appropriate in hardware, computer-executable instructions, firmware, or combinations thereof. Computer-executable instruction or firmware implementations of the processor(s) 454 may include computer-executable or machine-executable instructions written in any suitable programming language to perform the various functions described.

The memory 452 may store program instructions that are loadable and executable on the processor(s) 454, as well as data generated during the execution of these programs. Depending on the configuration and type of service provider computers 450, the memory 452 may be volatile (such as RAM) and/or non-volatile (such as ROM, flash memory, etc.). The service provider computers 450 may also include additional storage 456, which may include removable storage and/or non-removable storage. The additional storage 456 may include, but is not limited to, magnetic storage, optical disks and/or tape storage. The disk drives and their associated computer-readable media may provide non-volatile storage of computer-readable instructions, data structures, program modules, and other data for the computing devices. In some implementations, the memory 452 may include multiple different types of memory, such as SRAM, DRAM, or ROM.

The memory 452, the additional storage 456, both removable and non-removable, are all examples of computer-readable storage media. For example, computer-readable storage media may include volatile or non-volatile, removable or non-removable media implemented in any method or technology for storage of information such as computer-readable instructions, data structures, program modules, or other data. The memory 452 and the additional storage 456 are all examples of computer storage media. Additional types of computer storage media that may be present in the service provider computers 450 may include, but are not limited to, PRAM, SRAM, DRAM, RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by the service provider computers 450. Combinations of any of the above should also be included within the scope of computer-readable media.

Alternatively, computer-readable communication media may include computer-readable instructions, program modules, or other data transmitted within a data signal, such as a carrier wave, or other transmission. However, as used herein, computer-readable storage media does not include computer-readable communication media.

The service provider computers 450 may also contain communications connection(s) 458 that allow the service provider computers 450 to communicate with a stored database, another computing device or server, user terminals and/or other devices on the network(s) 418. The service provider computers 450 may also include I/O device(s) 460, such as a keyboard, a mouse, a pen, a voice input device, a touch input device, a display, speakers, a printer, etc.

Turning to the contents of the memory 452 in more detail, the memory 452 may include an operating system 462, one or more data stores 464, and/or one or more application programs, modules, or services for implementing the features disclosed herein, such as the features provided by the exercise recommendation engine 470.

Figure 5:
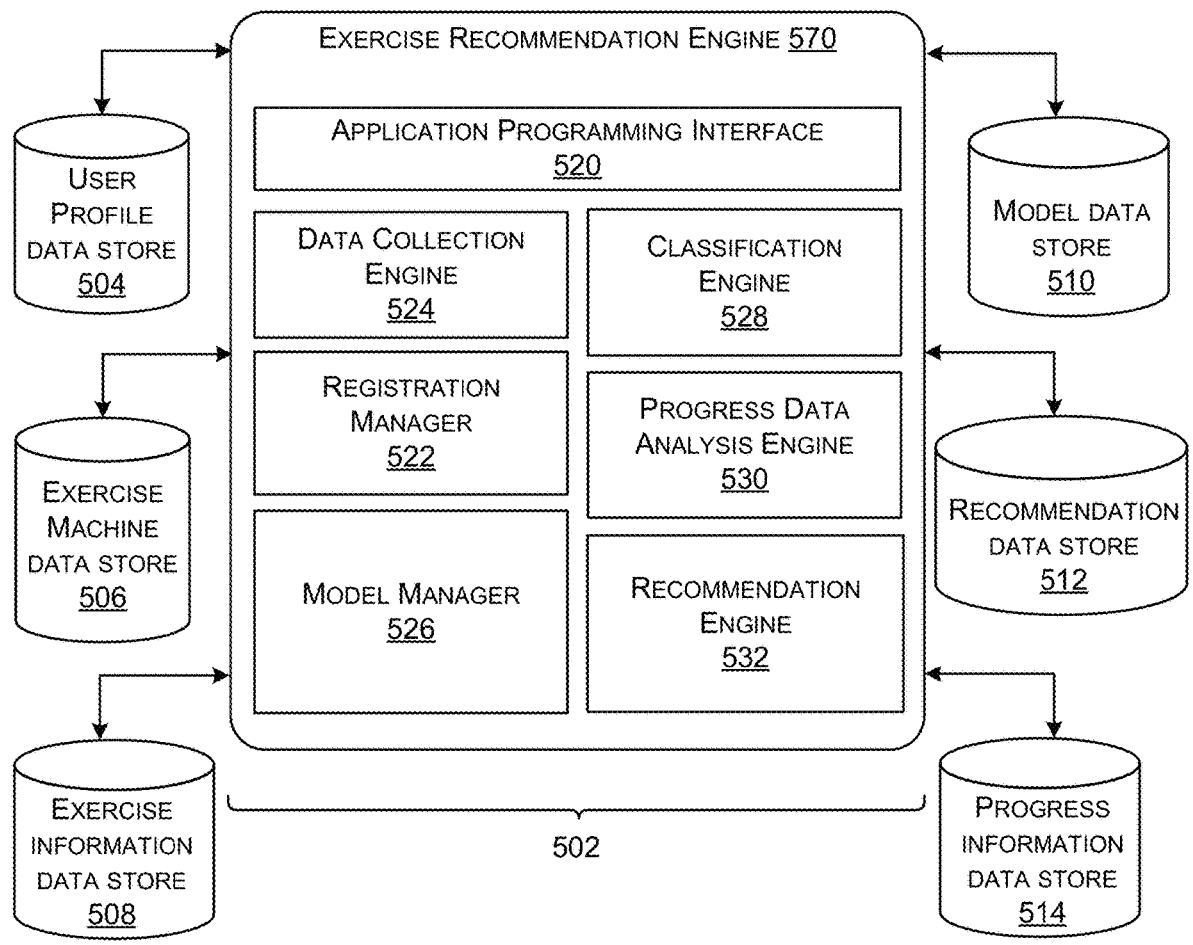
FIG. 5 is a simplified block diagram illustrating an example computer architecture for implementing the exercise recommendation engine discussed herein, according to at least one embodiment.

FIG. 5 is a simplified block diagram illustrating an example computer architecture 500 for an exercise recommendation engine (e.g., the exercise recommendation engine 470 of FIG. 4) discussed herein, according to at least one embodiment. The exercise recommendation engine 470 may include a plurality of modules 502 that may perform functions in accordance with at least one embodiment. The modules 502 may be software modules, hardware modules, or a combination thereof. If the modules 502 are software modules, the modules 502 can be embodied on a computer readable medium and processed by a processor in any of the computer systems described herein. It should be noted that any module or data store described herein, may be, in some embodiments, be a service responsible for managing data of the type required to make corresponding calculations. The modules 502 may be exist as part of the exercise recommendation engine 470 operating on the service provider computer(s) 450 of FIG. 4, or the modules may exist as separate modules or services external to the service provider computer(s) 450 (e.g., as part of the application 406 of FIG. 4 operating on the user device(s) 404 of FIG. 4 and/or as part of the application 432 of FIG. 4 operating on the exercise machine(s) 430 of FIG. 4.

In the embodiment shown in the FIG. 5, a user profile data store 504, an exercise machine data store 506, an exercise information data store 508, a model data store 510, a recommendation data store 512, and a progress information data store 514, are shown, although data can be maintained, derived, or otherwise accessed from various data stores, either remote or local to the exercise recommendation engine 470, to achieve the functions described herein. In at least one embodiment, the data stores described herein may be physically located on the user device(s) 404, the exercise machine(s) 430 or the service provider computers 450, for example, as part of an exercise recommendation service. The exercise recommendation engine 470, as shown in FIG. 5, includes various modules such as an application programming interface 520, a registration manager 522, a data collection engine 524, a model manager 526, a classification engine 528, a progress data analysis engine 530, and a recommendation engine 532. Some functions of the modules 520-532 are described below. However, for the benefit of the reader, a brief, non-limiting description of each of the modules is provided in the following paragraphs.

In at least one embodiment, the exercise recommendation engine 470 includes the application programming interface 520. Generally, the application programming interface 520 may be utilized to receive and/or provide any suitable information to and/or from the exercise recommendation engine 470 (or modules of the exercise recommendation engine 470) with respect to any example provided herein.

In at least one embodiment, the exercise recommendation engine 470 includes the registration manager 522. The registration manager 522 may be configured with instructions to implement various registration collection activities. For example, the registration manager 522 may be configured to host a website and/or network page (e.g., a registration interface) associated with the application 406 of FIG. 4 operating the user device(s) 404 of FIG. 4. The registration manager 522 may receive user input via the provided registration interface. By way of example, a user may utilize one of the user device(s) 404 and/or the exercise machine(s) 430 to input user-profile information via the provided registration interface. The registration manager 522 may be configured to receive such information (e.g., via the application programming interface 520) and store the received information within a record associated with a user (e.g., a user profile) within the user profile data store 504. At any suitable time, the user (e.g., the users 402) and/or a sensor (e.g., the sensor(s) 424) may provide updates to the user-profile information. The registration manager 522 may be configured to receive and process the received user-profile information such that the user profile is updated with the received user-profile information. In some embodiments, the registration manager 522 may be configured to cause the stored user-profile information to be presented via the I/O device(s) 408 and/or the I/O device(s) 434 of FIG. 4.

In at least one embodiment, the registration manager 522 may be configured to receive and process exercise machine registration information. Exercise machine registration information may include, but is not limited to an exercise machine identifier and any suitable characteristics of an exercise machine (e.g., make, model, serial number, machine settings information, machine capabilities information, and the like). The registration manager 522 may receive exercise machine registration information via the provided registration interface and/or the registration manager 522 may receive exercise machine registration information by other means (e.g., such as an automatic transmission upon startup of an exercise machine, as part of a configuration process associated with an exercise machine, etc.). The registration manager 522 may be configured to receive such information (e.g., via the application programming interface 520) and store the received information within a record associated with an exercise machine (e.g., an exercise machine profile) within the exercise machine data store 506. At any suitable time, the registration manager 522 may be configured to receive and process exercise machine information corresponding to updates to the exercise machine profile.

In at least one embodiment, the exercise recommendation engine 470 includes the data collection engine 524. The data collection engine 524 may be configured with instructions to implement various data collection activities. For example, the data collection engine 524 may be configured to receive and process exercise information associated with a user and/or an exercise machine. Exercise information may be provided via the application 432 and/or the sensor(s) 460. The data collection engine 524 may be configured to receive and maintain exercise information for one or more users within the exercise information data store 508, a data store configured to store such information. Additionally, or alternatively, the exercise information may be stored by the data collection engine 524 as part of the user profile associated with the user for which the exercise information is collected.

In at least one embodiment, the data collection engine 524 may be configured to receive and process vital sign information associated with a user. Vital sign information may be provided via the application 406, the sensor(s) 424, the application 432, the sensor(s) 460, or any suitable combination of the above. The data collection engine 524 may be configured to receive and store vital sign information associated with a user within the user's user profile.

In at least one embodiment, the exercise recommendation engine 470 includes the model manager 526. The model manager 526 may be configured with instructions that implement generation, training, and maintenance procedures for one or more machine-learning models (e.g., classification models). In at least one embodiment, the model manager 526 may be configured to execute one or more clustering algorithms to classify input data (e.g., vital sign information, user-profile information, exercise information, etc.) as belonging to a particular exercise category and/or sub-category.

In some embodiments, the model manager 526 may be configured to receive and store historical information associated with a number of users including historical exercise information, and/or user-profile information, and/or historical vital sign information. The historical information associated with the users may be associated with predetermined classifications (e.g., one or more exercise categories, one or more sub-categories, etc.). The model manager 526 may be configured to utilize the historical information in conjunction with one or more supervised learning algorithms in order to generate a classification model. The classification model generated may be configured to receive input data (e.g., exercise information, vital sign information, user profile information, etc.) and classify the input data as belonging to a one or more exercise categories and/or one or more sub-categories. In some embodiments, the model manager 526 may be configured to store one or more generated models (e.g., classification models) within the model data store 510.

Additional exercise information, vital sign information, and/or user-profile information may be received by the model manager 526. In some embodiments, the model manager 526 may be configured to receive such information (or obtain such information from the exercise information data store 508 and/or the user profile data store 504). Upon receipt, or at another suitable time, the model manager 526 may be configured to utilize the additional information to retrain one or more stored models. In some embodiments, the model manager 526 may be configured to identify a particular model from a set of previously generated models by utilizing the training data to determine which model provides the most accurate classifications.

In at least one embodiment, classification engine 528, a module of the exercise recommendation engine 470, may be configured to receive fitness-related information (e.g., exercise information, vital sign information, and/or user-profile information) related to a user and/or exercise machine. Such information may be received in real-time, or near real-time as the information is generated. In some embodiments, the classification engine 528 may be configured to utilize the model identified by the model manager 526 as providing the most accurate classifications. Using the identified model, the classification engine 528 may be configured to provide the received fitness-related information to the model as input. The classification engine 528 may be configured to receive and/or obtain a classification (e.g., an exercise category and/or sub-category) from output provided by the model. In some examples, the classification engine 528 may be configured to store the classification with the user-profile associated with the user.

In at least one embodiment, the progress data analysis engine 530, a module of the exercise recommendation engine 470, may be configured to maintain expected progress data within the progress information data store 514. Expected progress data may identify any suitable number of classification categories (e.g., one or more exercise categories) and/or sub-categories (e.g., one or more exercise levels). As described above, expected progress data may include rules that define relationships between categories, between sub-categories, and/or between categories and sub-categories. Expected progress data may further be associated with one or more goals (e.g., a fitness goal). In some examples, expected progress data may define a progress path that identifies a sequence (an order) by which categories/sub-categories) may be traversed in order to achieve a desired category/sub-category/goal. In some examples, the expected progress data may identify a progress path for a user to reach a category and/or sub-category (e.g., one that is associated with a particular goal), or a progress path that identifies a particular degree of improvement (e.g., an increase in level and/or category over a particular time).

In at least one embodiment, the recommendation engine 532, a module of the exercise recommendation engine 470, may be configured to maintain a database of recommendations (e.g., exercise-related recommendations, health/fitness-related recommendations, etc.). As described above, a recommendation can indicate to a user a change in a type of exercise machine utilized by a user and/or the manner in which a user utilizes a particular exercise machine. By way of example, a recommendation may suggest that the user increase or decrease speed on the currently utilized exercise machine. Another recommendation may suggest that the user utilize a different exercise machine than the one currently being utilized. Yet, another recommendation may suggest that the user increase or decrease weight and/or repetitions. The number and breadth of the recommendations provided may be ascertained by one skilled in the art. In some embodiments, recommendations may be associated with a category (e.g., an exercise category), a sub-category (e.g., beginning, intermediate, advanced, expert, etc.), and/or a fitness goal. Thus, in some embodiments, recommendations may be identified for a user based on matching a category and/or sub-category associated with the user (or user profile of the user), and/or a category/sub-category associated with a progress path identified for the user/user profile, to a category and/or sub-category associated with the recommendations.

In some examples, predefined recommendations may be received/obtained by the recommendation engine 532 and stored within the recommendation data store 512. Additionally, or alternatively, recommendations may be generated by the recommendation engine 532 according to expected progress data and stored within the recommendation data store 512.

By way of example, progress data may indicate that sub-category 2 follows sub-category 1. Additionally, progress data may indicate that a user associated with sub-category 1 can lift 15 pounds using a particular type of exercise machine, while a user associated with sub-category 2 can lift 30 pounds on the same type of exercise machine. In some examples, the recommendation engine 532 may generate a recommendation by determining an incremental plan to move the user from sub-category 1 to sub-category 2. As a non-limiting example, the recommendation engine 532 may be configured to determine a difference between the corresponding capabilities associated with each sub-category. In the ongoing example, the different would be determined to be a 15-pound weight difference. Given the difference of 15 pounds, the recommendation engine 532 may identify a predefined period of time (e.g., one month), or a period of time based on the difference (e.g., where a smaller period of time is used for a 15 pound difference than a period of time used for a 30 pound difference). The recommendation engine 532 may calculate incremental increases in lift weight based on the difference and the identified time period. Accordingly, the recommendation engine 532 may generate and store one or more recommendations that suggest weight increases according to the incremental increases. In some examples, the recommendation engine 532 may maintain a record identifying recommendations that have been provided to the user and, in some cases, the date and/or time at which the recommendations were provided. This record may be stored as part of the user profile associated with the user.

In some embodiments, progress of the user and/or effectiveness of the provided recommendation may be tracked. As discussed above, the data collection engine 524 may store updated user profile information associated with a user within the user-profile data store 504. Accordingly, changes to the user's physical appearance (e.g., weight, body measurements, etc.) may be ascertained from the user's profile. Additionally, exercise information associated with the user may be maintained within the exercise information data store 508. Accordingly, a historical record of exercise information associated with the user is maintained. User-profile information may be collected via user-input or automatically by a user device and/or an exercise machine in any suitable manner.

In some embodiments, a user may be provided a customized recommendation (e.g., by the recommendation engine 532) and the user's subsequent exercise information may be tracked to determine whether the user performed an action associated with the provided recommendation. By way of example, the recommendation engine 532 may provide the user (e.g., via the user device(s) 404 and/or the exercise machine(s) 430) a customized recommendation that suggests increasing the speed on a treadmill, the exercise information collected for the user (e.g., by the data collection engine 524) may be analyzed to determine that the user did (or did not) increase the speed of the treadmill as suggested. If the user did perform the action suggested (e.g., increased treadmill speed), then subsequent exercise information may be analyzed and attributed to the provided recommendation.

In some embodiments, the recommendation engine 532 may be configured to analyze subsequent exercise information (e.g., duration for which the user can run on a treadmill at a given speed), changes in user-profile information (e.g., weight, flexibility, etc.), vital sign information of the user, or any suitable information to determine that the recommendation resulted in the user progressing within some threshold of a determined progress path. That is, the recommendation engine 532 may be configured to access progress data and/or an identified progress path associated with the user. If the progress data/path indicates that the user is supposed to be able to run at a particular speed (e.g., 3.5 miles per hour) for a particular duration (e.g., 30 minutes), within the next month, the user's exercise information may be tracked to determine that the user is progressing toward that ability. Based on a determination that the user is progressing in according with the identified progress path, the recommendation engine 532 may configured to associate the recommendation as being effective. In some embodiments, the recommendation engine 532 may be configured to assign a label, a score, or the like, that indicates a degree of effectiveness for the recommendation. Accordingly, when providing recommendations to a user, the recommendation engine 532 may utilize recommendation scores/labels to identify effective (or the most-effective) recommendation(s) for those users.

In some embodiments, the recommendation engine 532 may be configured to utilize exercise machine information (e.g., obtained from the exercise machine data store) to identify a particular recommendation from the recommendation data store 512. By way of example, the recommendation engine 532 may obtain exercise machine information corresponding to an exercise machine with which the user is interacting. The exercise machine information may, in some examples, indicate one or more settings and/or one or more machine capabilities of the exercise machine. The recommendation engine 532 may utilize the exercise machine information to identify any candidate recommendations that may be incapable of being performed with the exercise machine. These recommendations may be filtered by the recommendation engine 532 such that a recommendation provided to the user does not suggest actions that are incapable of being performed with the exercise machine currently being utilized by the user.

Figure 6:
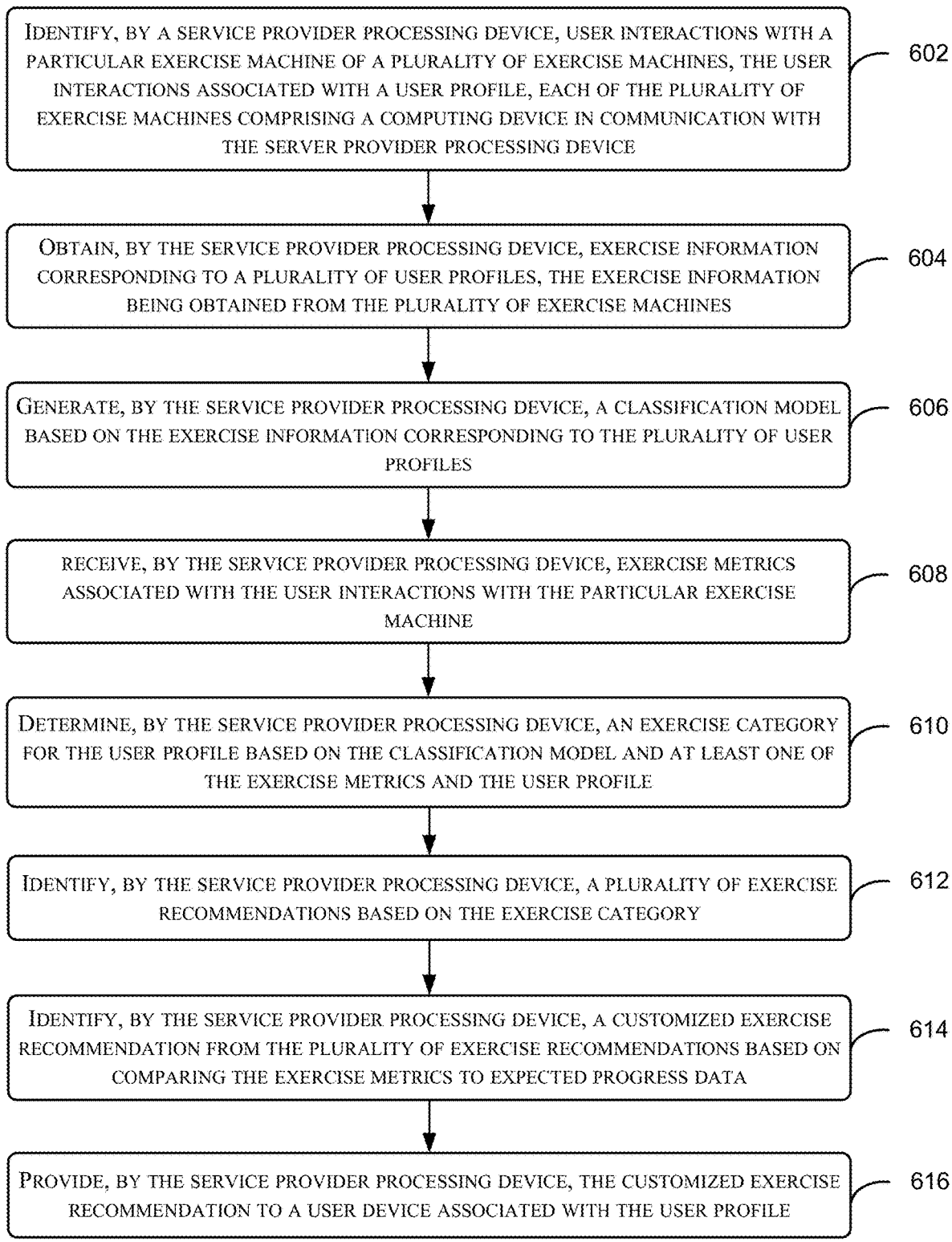
FIG. 6 is a simplified flow diagram illustrating an example process for providing a customized exercise-related recommendation utilizing the exercise recommendation engine discussed herein, according to at least one example.
Figure 7:
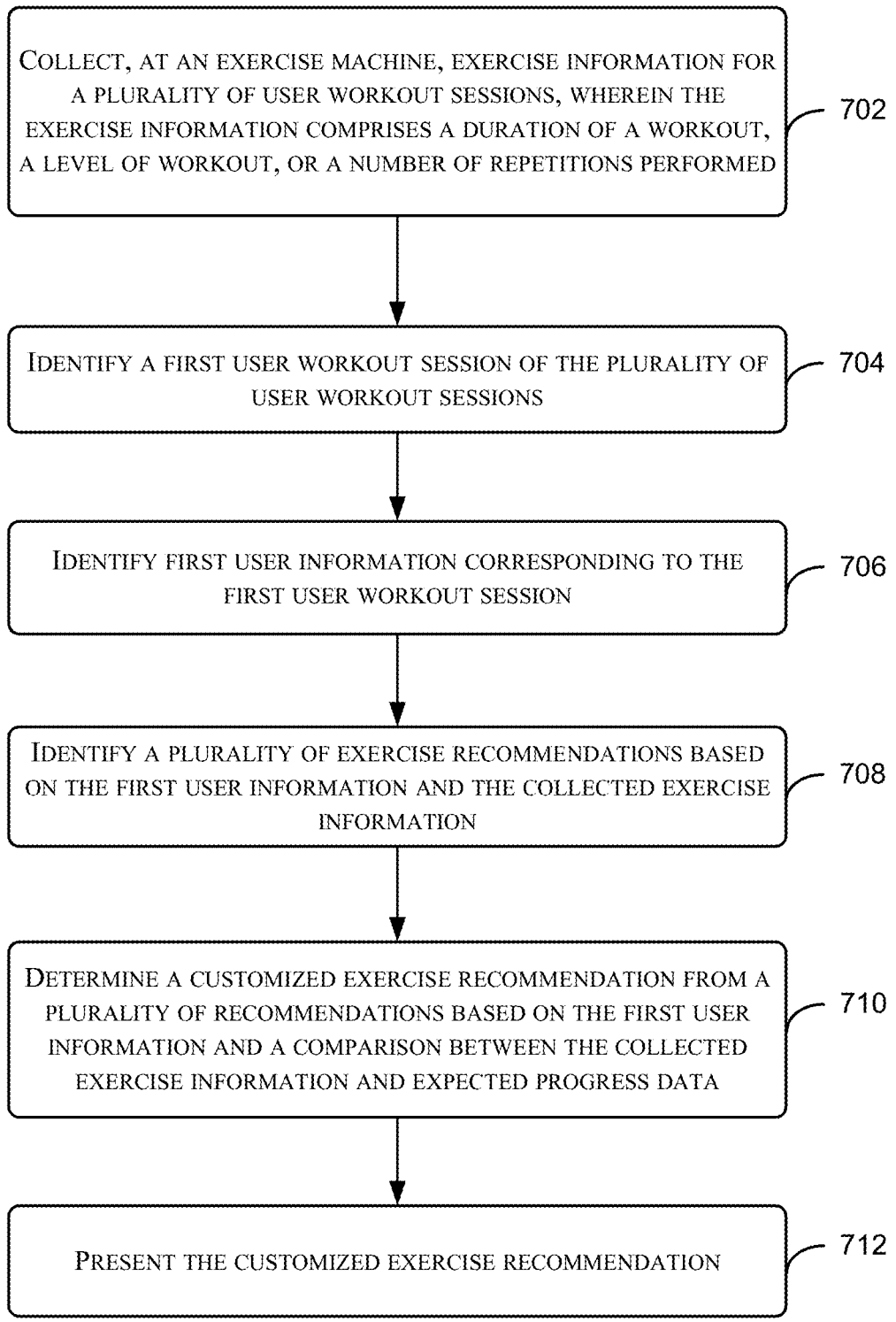
FIG. 7 is another simplified flow diagram illustrating another example process for providing a customized exercise-related recommendation utilizing the exercise recommendation engine discussed herein, according to at least one example.
Figure 8:
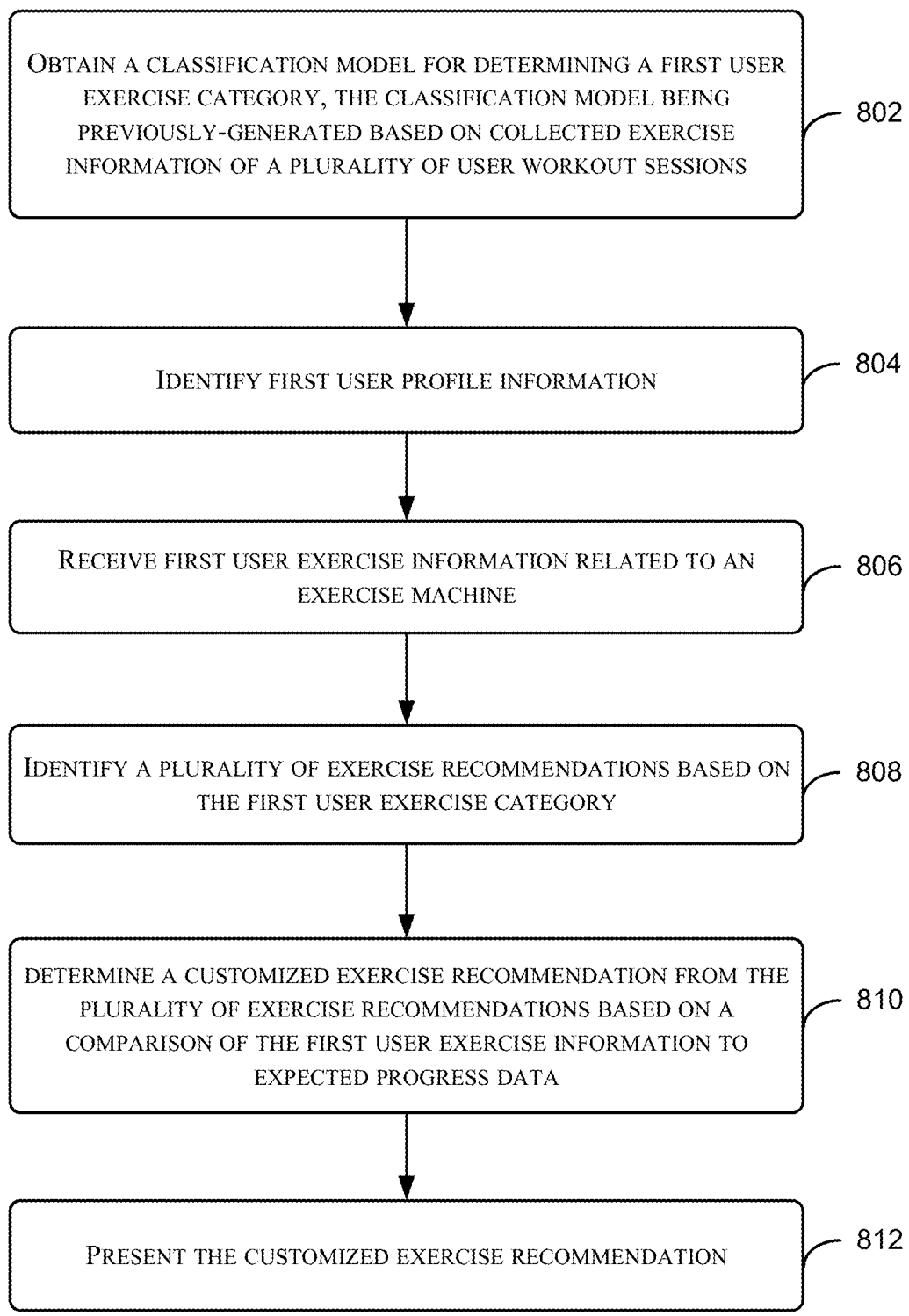
FIG. 8 is yet another simplified flow diagram illustrating yet another example process for providing a customized exercise-related recommendation utilizing the exercise recommendation engine discussed herein, according to at least one example.

FIGS. 6-8 illustrate example flow diagrams showing respective processes 600, 700, and 800 for providing a customized exercise-related recommendation utilizing the exercise recommendation engine discussed herein. These processes 600, 700, and 800 are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes described herein.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

In some examples, the process 600 may be performed by the exercise recommendation engine 470, operating on the service provider computers 450 of FIG. 4 (referred to as a server provider processing device). The process 600 may begin at 602 where user interactions with a particular exercise machine of a plurality of exercise machines may be identified by a service provider processing device. In some embodiments, the user interactions may be associated with a user profile. In some embodiments, each of the plurality of exercise machines may comprise a computing device in communication with the server provider processing device. By way of example, user interactions may include bringing a user device within a threshold distance of an exercise machine, remaining within a threshold distance to the exercise machine, performing an action with the exercise machine, logging in to an exercise machine, and the like.

At block 604, exercise information (or other fitness-related information) corresponding to a plurality of user profiles (e.g., corresponding to the users 106, the user(s) 402, etc.) may be obtained by the service provider processing device. In some embodiments, the exercise information (or other fitness-related information) may be obtained from the plurality of exercise machines.

At block 606, a classification model may be generated (e.g., by the service provider processing device). In some embodiments, the classification model may be generated based on the exercise information corresponding to the plurality of user profiles. Generation may occur as described herein, by utilizing collected fitness-related information as training data and a supervised machine-learning algorithm.

At block 608, exercise metrics (e.g., exercise information) associated with the user interactions with the particular exercise machine may be received (e.g., by the service provider processing device).

At block 610, an exercise category for the user profile may be determined (e.g., by the service provider processing device) based on the classification model and at least one of the exercise metrics (exercise information) and the user profile (user profile information).

At block 612, a plurality of exercise recommendations may be identified (e.g., by the service provider processing device) based on the exercise category. As described above, a category/sub-category corresponding to the user/user profile may be matched to a category/sub-category associated with individual recommendations. The recommendation(s) having the same category/sub-category may be utilized as candidate recommendations from which a customized recommendation may be identified/selected.

At block 614, a customized exercise recommendation may be identified (e.g., by the service provider processing device) from the plurality of exercise recommendations based on comparing the exercise metrics (exercise information) to expected progress data. By way of example, a comparison of the exercise metrics to the expected progress data may indicate a need for improvement in a specific area (e.g., speed, stamina, weight training, etc.). Recommendations may additionally be associated with such attributes such that a customized exercise recommendation may be selected that relates to the specific area of improvement.

At block 616, the customized exercise recommendation may be provided (e.g., by the service provider processing device) to a user device associated with the user profile.

In some examples, the process 700 may be performed by the exercise recommendation engine 470 (e.g., operating in whole, or in part, on any suitable combination of the user device(s) 404, the exercise machine(s) 430, and/or the service provider computers 450). The process 700 may be performed by a system comprising a plurality of exercise machines individually configured with one or more sensors, one or more data networks, one or more processors, and one or more memories storing computer-readable instructions that, upon execution by the one or more processors, cause the system to perform the process 700. The process 700 may begin at 702 where exercise information (or other fitness-related information) for a plurality of user workout sessions may be collected (e.g., at an exercise machine). In some embodiments, the exercise information may comprise a duration of a workout, a level of workout, or a number of repetitions performed.

At block 704, a first user workout session of the plurality of user workout sessions may be identified. The first user workout session may relate to a first user. The first user may be one of the plurality of users corresponding to the plurality of user workout sessions, or the first user may be separate from the plurality of users.

At block 706, first user information corresponding to the first user workout session may be identified. First user information may include fitness-related information such as user profile information, exercise information, and/or vital sign information.

At block 708, a plurality of exercise recommendations may be identified based on the first user information and the collected exercise information. As described above, a plurality of exercise recommendations (candidate recommendations) may be identified by classifying the user/user profile using fitness-related information as input to a classification model. Once the input is classified, the category/sub-category of the input is matched to the category/sub-category of recommendations contained in a recommendation database. Recommendations with a matching category/sub-category may be utilized as candidate recommendations from which a customized exercise-related recommendation may be identified.

At block 710, a customized exercise recommendation may be determined from a plurality of recommendations based on the first user information and a comparison between the collected exercise information and expected progress data. As described above, a comparison of the first user information (e.g., fitness-related information of a first user such as user-profile information of the first user) to the expected progress data may indicate a need for improvement in a specific area (e.g., speed, stamina, weight training, etc.). Recommendations may additionally be associated with such attributes such that a customized exercise recommendation may be selected so that it relates to the specific area of improvement identified.

At block 712, the customized exercise recommendation may be presented. In some examples, the customized exercise recommendation may be presented on a user device, an exercise machine, or a suitable combination of the two.

In some examples, the process 800 may be performed by the exercise recommendation engine 470 (e.g., operating in whole, or in part, on any suitable combination of the user device(s) 404, the exercise machine(s) 430, and/or the service provider computers 450). In some embodiments, a computer-readable storage medium comprising computer-readable instructions may, upon execution by one or more processors, cause the one or more processors to perform the process 800. The process 800 may begin at 802 where a classification model for determining a first user exercise category may be obtained. In some embodiments, the classification model may be previously-generated based on collected exercise information of a plurality of user workout sessions.

At block 804, first user profile information may be identified. First user-profile information (user-profile information associated with a first user) may be received as user input and may include any suitable information associated with a user including, but is not limited to, physical characteristics (weight, height, body type, physical disability, dietary/nutritional considerations, general activity level (e.g., sedentary, active), etc.) demographic information (e.g., age, gender, ethinicity, etc.), medical information (e.g., a medical diagnosis, a medication currently being taken, a dosage for such medication(s), a genetic disposition to a particular disease/disorder, etc.), goal information (e.g., identifying one or more fitness goals such as running a full marathon, building strength in a particular muscle group, physical therapy goals, running a 5K, being able to run for 30 minutes straight, running a mile in under 6 minutes, etc.), and the like.

At block 806, first user exercise information related to an exercise machine may be received. First user exercise information (exercise information associated with a first user) may include any suitable data obtainable from one or more sensors (e.g., an accelerometer, a gyroscrope, a camera, etc.) attached to, or otherwise in communication with, an exercise machine or user device (e.g., a body-worn device, a cellphone, etc.), machine identification data (e.g., a machine identifier), or any suitable information related to an exercise machine and/or a measure corresponding to an exercise performed at the exercise machine. First user exercise information may be utilized to determine a myriad of metrics such as a speed, an amount of weight being lifted, a range of motion associated with a part of an exercise machine, an amount of shaking associated with one or more parts of the exercise machine and/or the first user, a number of repititions performed, and the like.

At block 808, a plurality of exercise recommendations may be identified based on the first user exercise category. As described above, the first user exercise category (e.g., a category/sub-category associated with the first user/the first user's profile) may be matched to the category/sub-category of recommendations contained in a recommendation database. Recommendations with a matching category/sub-category (e.g., the plurality of exercise recommendations) may be utilized as candidate recommendations from which a customized exercise-related recommendation may be identified.

At block 810, a customized exercise recommendation may be determined from the plurality of exercise recommendations based on a comparison of the first user exercise information to expected progress data. As described above, a comparison of the first user exercise information (e.g., exercise information of a first user) to the expected progress data may indicate a need for improvement in a specific area (e.g., speed, stamina, weight training, etc.). Recommendations may additionally be associated with such attributes such that a customized exercise recommendation may be selected so that it relates to the specific area of improvement identified. In at least one example, the plurality of exercise recommendations may be scored/ranked according to a relevancy score and/or degree of improvement related to the area of improvement identified.

At block 812, the customized exercise recommendation may be presented. In some examples, the customized exercise recommendation may be presented on a user device, an exercise machine, or a suitable combination of the two.

What is claimed is:

1. A non-transitory computer-readable storage medium comprising computer-readable instructions that, upon execution by one or more processors of a service provider processing device, cause the one or more processors to perform operations comprising:
    training a classification model based at least in part on exercise information of a plurality of user workout sessions associated with a plurality of user profiles, wherein training the classification model comprises:
        using a cluster analysis algorithm to cluster the exercise information into a plurality of clusters;
        assigning a classification to each cluster of the plurality of clusters; and
        using the classification of each cluster as training data to train the classification model using a supervised machine-learning algorithm;
    receiving user exercise information associated with a user profile;
    classifying the user exercise information into an exercise category of a plurality of exercise categories using the classification model;
    generating a customized progress path associated with the exercise category and a user expertise level of the user profile corresponding to the exercise category;
    identifying a plurality of exercise recommendations based at least in part on the exercise category;
    determining a customized exercise recommendation from the plurality of exercise recommendations based at least in part on the user exercise information and the customized progress path;
    providing the customized exercise recommendation to a user device associated with the user profile;
    retraining, based at least in part on adding the customized exercise recommendation to the training data, the classification model to define a retrained classification model; and
    providing a subsequent customized exercise recommendation to the user device based at least in part on the retrained classification model.

2. The non-transitory computer-readable storage medium of claim 1, wherein the exercise information comprises sensor data collected from a plurality of exercise machines, wherein the plurality of exercise machines are used by a plurality of users associated with the plurality of user profiles during the plurality of user workout sessions.

3. The non-transitory computer-readable storage medium of claim 1, wherein retraining the classification model further comprises:
    receiving subsequent user exercise information of a different plurality of user workout sessions; and
    retraining the classification model based at least in part on the subsequent user exercise information.

4. The non-transitory computer-readable storage medium of claim 3, comprising further instructions that cause the one or more processors to perform operations comprising providing, a different customized exercise recommendation to an additional user device associated with an additional user profile of the plurality of user profiles based at least in part on the retrained classification model.

5. The non-transitory computer-readable storage medium of claim 1, comprising further instructions that cause the one or more processors to perform operations comprising generating a customized exercise plan based at least in part on the exercise information, user profile information associated with the user profile, the exercise category, and the customized progress path, wherein the customized exercise recommendation corresponds to the customized exercise plan.

6. The non-transitory computer-readable storage medium of claim 1, wherein the user exercise information comprises first user exercise information, and wherein retraining the classification model comprises:
   detecting, based at least in part on second user exercise information, instances in which the first user exercise information no longer match the customized progress path; and
   responsive to detecting the instances, retraining, the classification model to define the retrained classification model based at least in part on the second user exercise information.

7. The non-transitory computer-readable storage medium of claim 1, wherein generating the customized progress path is based at least in part on a user fitness goal.

8. The non-transitory computer-readable storage medium of claim 7, wherein generating the customized progress path includes:
   determining a customized progression of a plurality of user expertise levels associated with the exercise category and a user fitness goal; and
   determining one or more target time periods corresponding to the plurality of user expertise levels.

9. The non-transitory computer-readable storage medium of claim 1, wherein the user exercise information includes one or more types of medical information associated with the user profile, wherein the one or more types of medical information includes at least a medical diagnosis or a medication.

10. The non-transitory computer-readable storage medium of claim 1, wherein the training data comprises instances of historical exercise information that are individually associated with a predetermined corresponding exercise category.

11. A computer-implemented method, comprising:
   training a classification model based at least in part on exercise information of a plurality of user workout sessions associated with a plurality of user profiles, wherein training the classification model comprises:
      using a cluster analysis algorithm to cluster the exercise information into a plurality of clusters;
      assigning a classification to each cluster of the plurality of clusters; and
      using the classification of each cluster as training data to train the classification model using a supervised machine-learning algorithm;
   receiving user exercise information associated with a user profile;
   classifying the user exercise information into an exercise category of a plurality of exercise categories using the classification model;
   generating a customized progress path associated with the exercise category and a user expertise level of the user profile corresponding to the exercise category;
   identifying a plurality of exercise recommendations based at least in part on the exercise category;
   determining a customized exercise recommendation from the plurality of exercise recommendations based at least in part on the user exercise information and the customized progress path;
   providing the customized exercise recommendation to a user device associated with the user profile;
   retraining, based at least in part on adding the customized exercise recommendation to the training data, the classification model to define a retrained classification model; and
   providing a subsequent customized exercise recommendation to the user device based at least in part on the retrained classification model.

12. The computer-implemented method of claim 11, wherein the exercise information comprises sensor data collected from a plurality of exercise machines, wherein the plurality of exercise machines are used by a plurality of users associated with the plurality of user profiles during the plurality of user workout sessions.

13. The computer-implemented method of claim 11, wherein retraining the classification model comprises:
   receiving subsequent user exercise information of a different plurality of user workout sessions; and
   retraining the classification model based at least in part on the subsequent user exercise information.

14. The computer-implemented method of claim 13, further comprising providing a different customized exercise recommendation to an additional user device associated with an additional user profile of the plurality of user profiles based at least in part on the retrained classification model.

15. The computer-implemented method of claim 11, further comprising generating a customized exercise plan based at least in part on the exercise information, user profile information associated with the user profile, the exercise category, and the customized progress path, wherein the customized exercise recommendation corresponds to the customized exercise plan.

16. The computer-implemented method of claim 11, wherein the user exercise information comprises first user exercise information, and wherein retraining the classification model comprises:
   detecting, based at least in part on second user exercise information, instances in which the first user exercise information no longer match the customized progress path; and
   responsive to detecting the instances, retraining, the classification model to define the retrained classification model based at least in part on the second user exercise information.

17. A system, comprising:
   one or more processors; and
   one or more memories storing computer-readable instructions that, upon execution by the one or more processors, cause the system to at least:
      train a classification model based at least in part on exercise information of a plurality of user workout sessions associated with a plurality of user profiles, wherein training the classification model comprises:
         using a cluster analysis algorithm to cluster the exercise information into a plurality of clusters;
         assigning a classification to each cluster of the plurality of clusters; and
         using the classification of each cluster as training data to train the classification model using a supervised machine-learning algorithm;

receive user exercise information associated with the user profile;

classify the user exercise information into an exercise category of a plurality of exercise categories using the classification model;

generate a customized progress path associated with the exercise category and a user expertise level of the user profile corresponding to the exercise category;

identify a plurality of exercise recommendations based at least in part on the exercise category;

determine a customized exercise recommendation from the plurality of exercise recommendations based at least in part on the user exercise information and the customized progress path;

provide the customized exercise recommendation to a user device associated with the user profile;

retrain, based at least in part on adding the customized exercise recommendation to the training data, the classification model to define a retrained classification model; and provide a subsequent customized exercise recommendation to the user device based at least in part on the retrained classification model.

18. The system of claim 17, wherein training the classification model comprises:
   receiving subsequent user exercise information of a different plurality of user workout sessions; and
   retraining the classification model based at least in part on the subsequent user exercise information.

19. The system of claim 18, wherein the one or more memories store additional instructions that, when executed by the one or more processors, cause the system to at least provide a different customized exercise recommendation to an additional user device associated with an additional user profile of the plurality of user profiles based at least in part on the retrained classification model.

20. The system of claim 17, wherein the user exercise information comprises first user exercise information, and wherein retraining the classification model comprises:
   detect, based at least in part on second user exercise information, instances in which the first user exercise information no longer match the customized progress path; and
   responsive to detecting the instances, retrain, the classification model to define the retrained classification model based at least in part on the second user exercise information.

* * * * *